(12) United States Patent
Hibner et al.

(10) Patent No.: US 7,419,472 B2
(45) Date of Patent: Sep. 2, 2008

(54) BIOPSY INSTRUMENT WITH INTERNAL SPECIMEN COLLECTION MECHANISM

(75) Inventors: John Hibner, Maineville, OH (US); Salvatore Privitera, Mason, OH (US); Thomas W. Huitema, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 491 days.

(21) Appl. No.: 10/676,944

(22) Filed: Sep. 30, 2003

(65) Prior Publication Data

US 2005/0215921 A1    Sep. 29, 2005

(51) Int. Cl.
*A61B 10/00* (2006.01)
*A61B 17/32* (2006.01)
*A61B 17/14* (2006.01)

(52) U.S. Cl. .................. 600/564; 600/562; 600/565; 600/566; 600/567; 600/568; 606/167; 606/170; 606/171; 606/184

(58) Field of Classification Search ............... 600/562, 600/564, 565, 566, 567, 568; 606/167, 170, 606/171, 184
See application file for complete search history.

(56) References Cited

U.S. PATENT DOCUMENTS

| | | | |
|---|---|---|---|
| 5,573,008 A * | 11/1996 | Robinson et al. | 600/567 |
| 5,601,585 A | 2/1997 | Banik et al. | |
| 5,649,547 A * | 7/1997 | Ritchart et al. | 600/566 |
| 6,019,733 A | 2/2000 | Farascioni | |
| 6,220,248 B1 * | 4/2001 | Voegele et al. | 128/898 |
| 6,428,486 B2 * | 8/2002 | Ritchart et al. | 600/566 |
| 6,432,064 B1 * | 8/2002 | Hibner et al. | 600/564 |
| 6,485,436 B1 | 11/2002 | Truckai et al. | |
| 2002/0183715 A1 * | 12/2002 | Mantell et al. | 604/506 |

* cited by examiner

*Primary Examiner*—Max Hindenburg
*Assistant Examiner*—Jeffrey G Hoekstra
(74) *Attorney, Agent, or Firm*—Gerry Gressel

(57) ABSTRACT

A biopsy instrument with an internal specimen collection mechanism is provided.

15 Claims, 22 Drawing Sheets

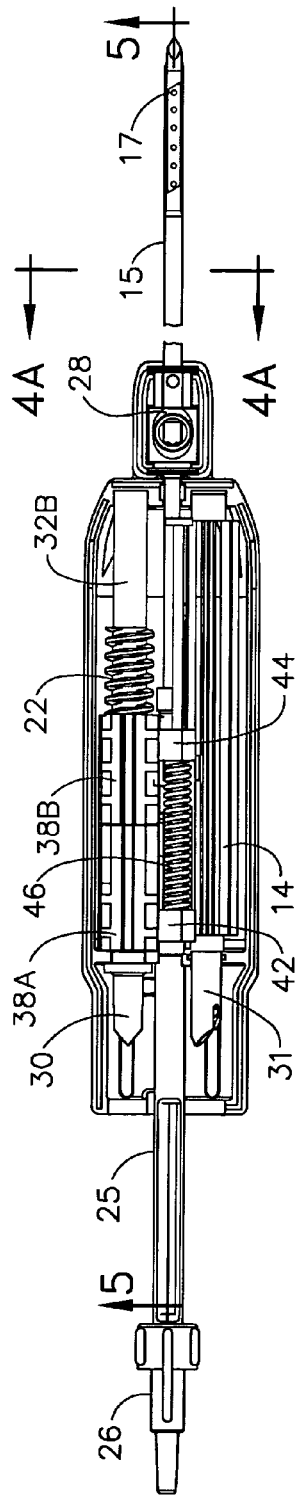
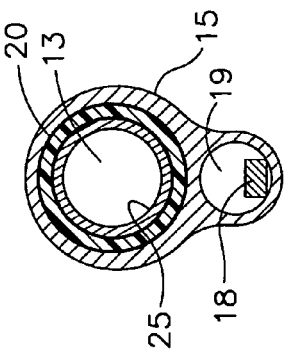
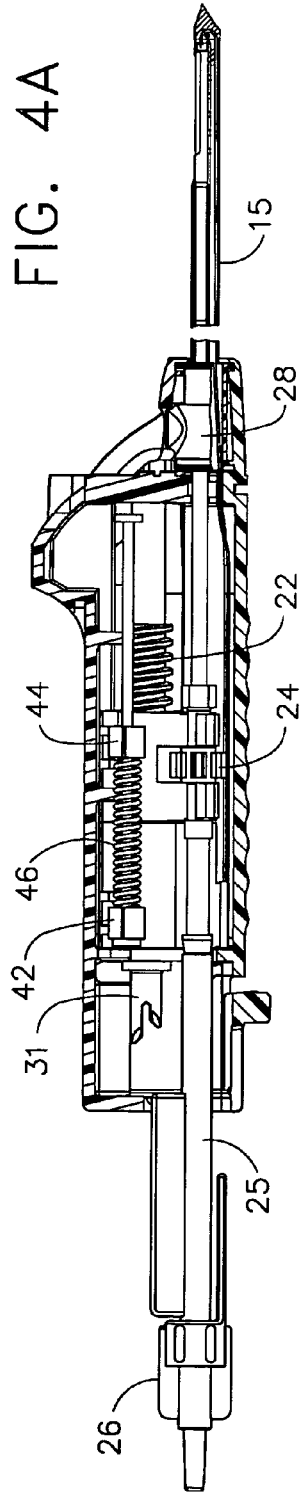
FIG. 4
FIG. 4A
FIG. 5

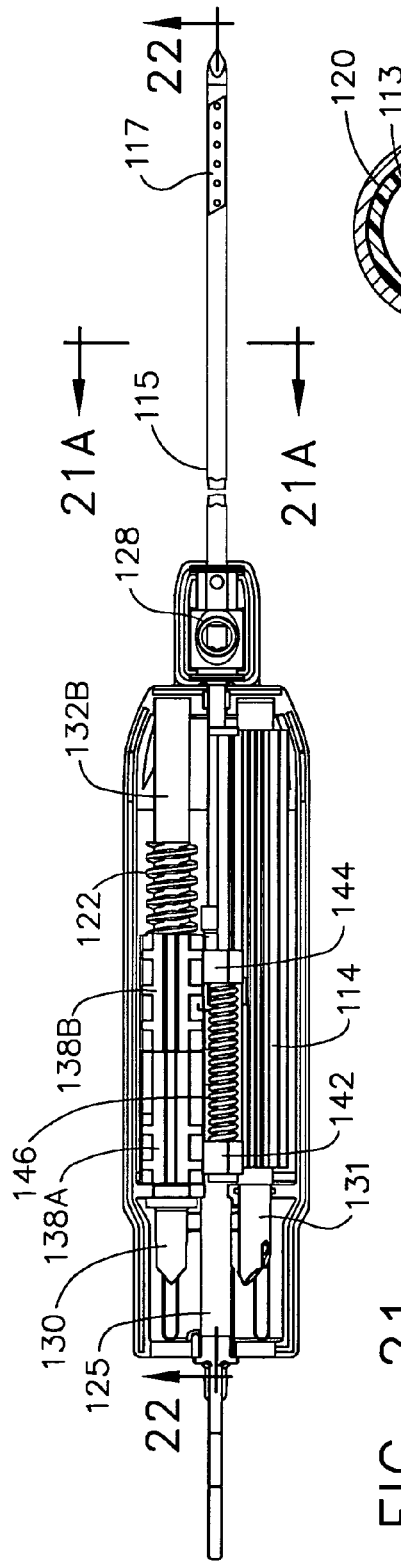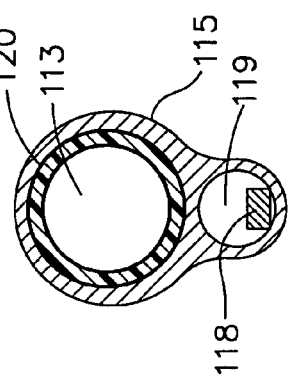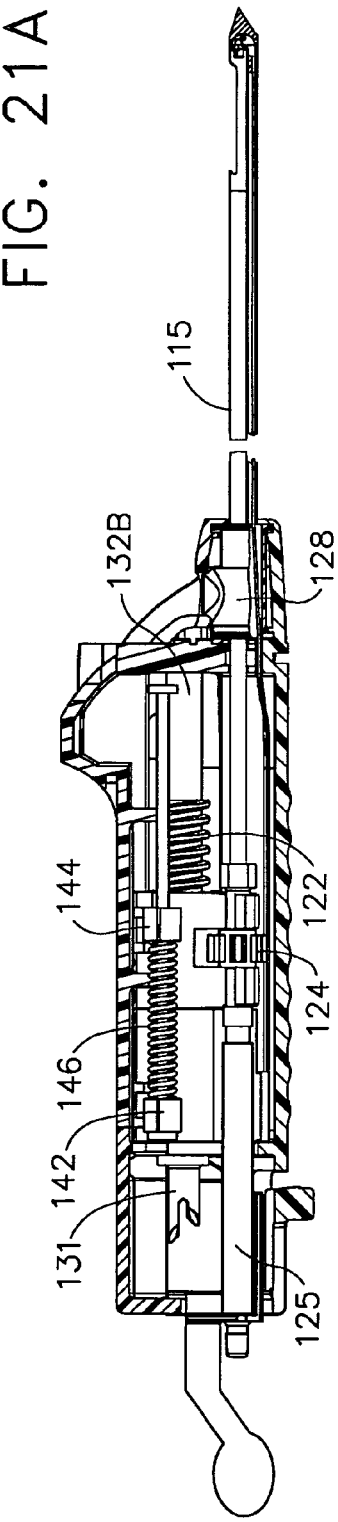
FIG. 21
FIG. 21A
FIG. 22

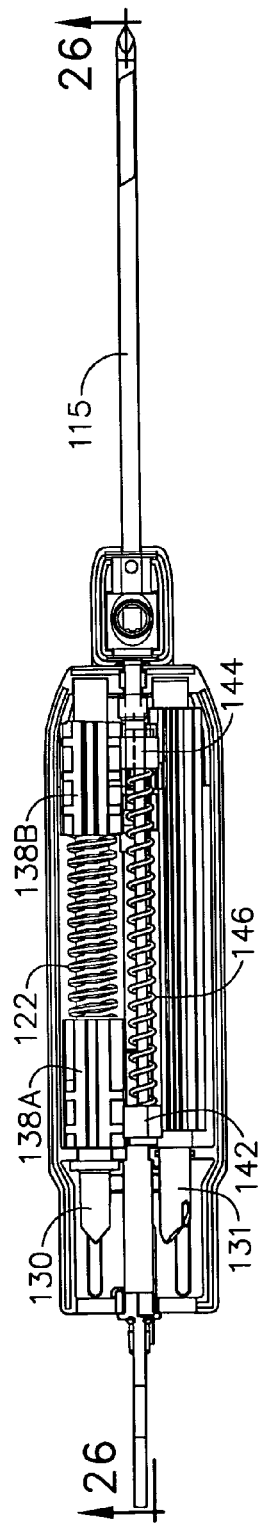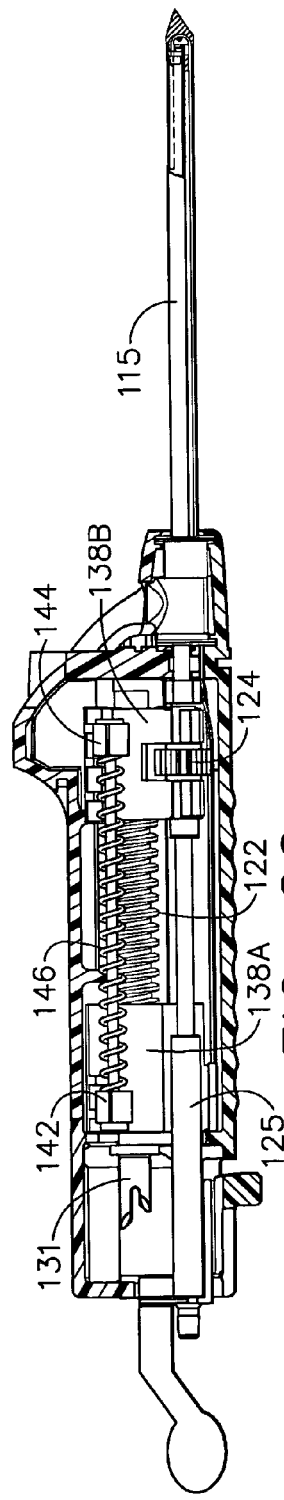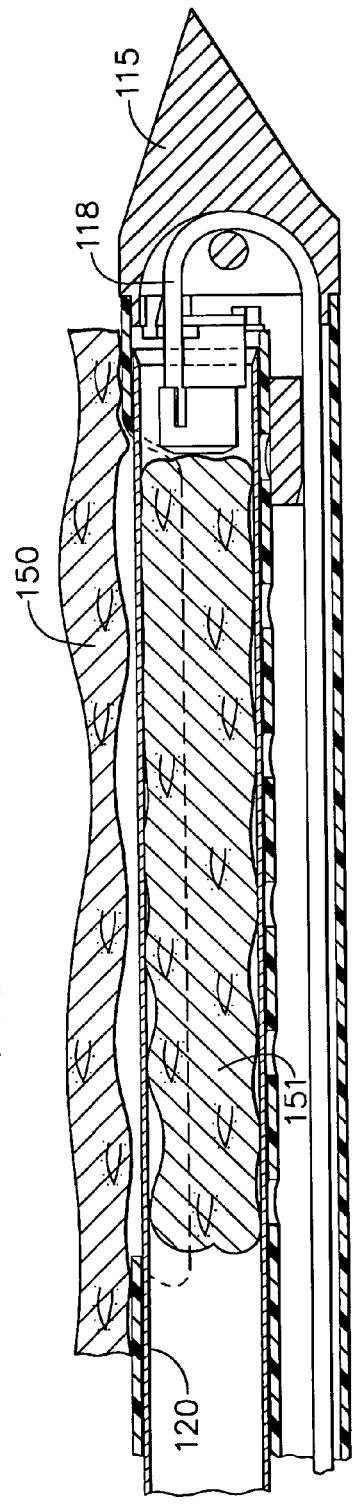

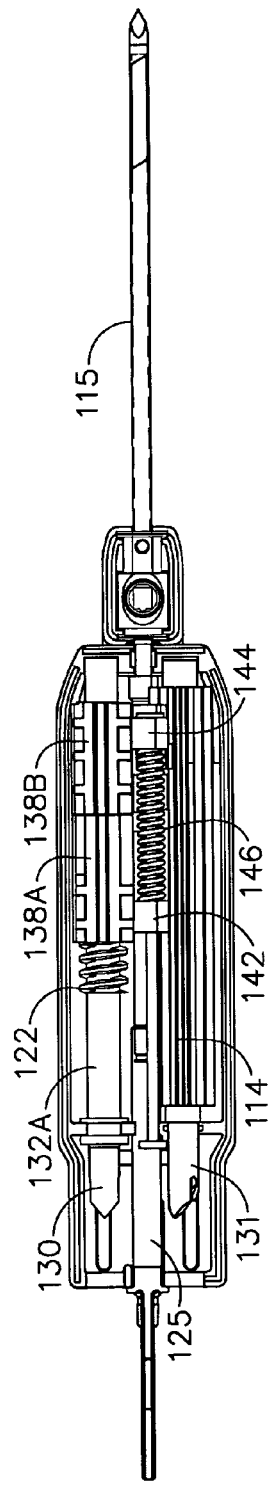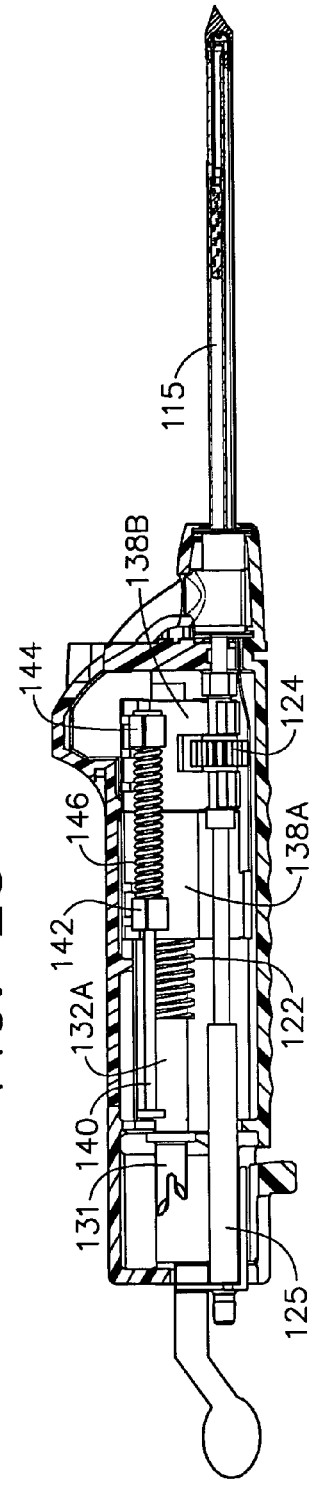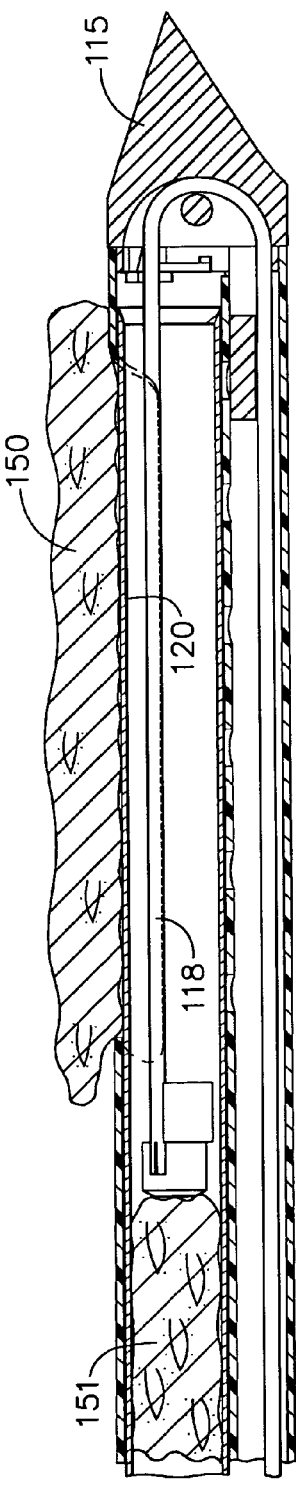

BIOPSY INSTRUMENT WITH INTERNAL SPECIMEN COLLECTION MECHANISM

FIELD OF THE INVENTION

The present invention generally relates to instruments for surgically sampling living tissue. More particularly the present invention relates to an improved biopsy probe for acquiring subcutaneous biopsies and/or removing lesions etc.

BACKGROUND OF THE INVENTION

The diagnosis and treatment of patients with cancerous tumors, pre-malignant conditions, and other disorders has long been an area of intense investigation. Non-invasive methods for examining tissue include palpation, X-ray, MRI, CT, and ultrasound imaging. When the physician suspects that a tissue may contain cancerous cells, a biopsy may be done using either an open procedure or a percutaneous procedure. For an open procedure, a scalpel is used by the surgeon to create a large incision in the tissue in order to provide direct viewing and access to the tissue mass of interest. The entire mass (excisional biopsy) or a part of the mass (incisional biopsy) may then be removed. For a percutaneous biopsy, a needle-like instrument is used through a very small incision to access the tissue mass of interest and to obtain a tissue sample for later examination and analysis. The advantages of the percutaneous method as compared to the open method may be significant and may include: less recovery time for the patient, less pain, less surgical time, lower cost, and less disfigurement of the patient's anatomy. Use of the percutaneous method in combination with imaging devices such as X-ray and ultrasound has resulted in highly reliable diagnoses and treatments.

Generally there are two ways to obtain percutaneously a portion of tissue from within the body, by aspiration or by core sampling. Aspiration of the tissue through a fine needle requires the tissue to be fragmented into pieces small enough to be withdrawn in a fluid medium. The method is less intrusive than other known sampling techniques, but one can only examine cells in the liquid (cytology) and not the cells and the structure (pathology). In core biopsy, a core or fragment of tissue is obtained for histologic examination, which may be done via a frozen or paraffin section.

The type of biopsy used depends mainly on various factors present in the patient, and no single procedure is ideal for all cases. Core biopsy, however, is very useful in a number of conditions and is widely used by physicians.

A number of biopsy devices have been designed and commercialized for use in combination with imaging devices. One such biopsy instrument is the BIOPTY® gun, available from C.R. Bard, Inc. and described in U.S. Pat. Nos. 4,699,154 and 4,944,308 as well as in U.S. Reissued Pat. No. Re. 34,056. The BIOPTY® gun is a core sampling biopsy device in which the biopsy needle is spring-powered. However, when using the BIOPTY® gun, the breast or organ must be punctured and the device is re-inserted each time a sample is taken. Another core biopsy device is the TRUE CUT® needle manufactured by Travenol Laboratories. This TRUE CUT® needle collects a single core of tissue using a pointed element with a side-facing notch to receive tissue and an outer, sharpened sliding cannula to cut the core sample from the surrounding tissue.

Aspiration biopsy devices for obtaining biopsy samples from the body are described in the following: U.S. Pat. No. 5,492,130; U.S. Pat. No. 5,526,821; U.S. Pat. No. 5,429,138; and U.S. Pat. No. 5,027,827. These patents describe devices, which use the aspiration method of liquid suspended tissue extraction rather than core sampling to extract tissue.

To overcome operator error associated with such devices, and to enable multiple sampling of the tissue without having to reenter the tissue for each sample, a biopsy instrument now marketed under the trade name MAMMOTOME™ was developed by Ethicon Endo-Surgery, Inc. The following patent documents disclose various biopsy devices and are incorporated herein by reference in their entirety: U.S. Pat. Nos. 6,273,862; 6,231,522; 6,228,055; 6,120,462; 6,086,544; 6,077,230; 6,017,316; 6,007,497; 5,980,469; 5,964,716; 5,928,164; 5,775,333; 5,769,086; 5,649,547 and 5,526,822. The MAMMOTOME™ instrument is a type of image-guided, percutaneous, coring, breast biopsy instrument. It is vacuum-assisted and some of the steps for retrieving the tissue samples have been automated. The physician uses this device to capture "actively" (using the vacuum) the tissue prior to severing it from the body. This allows for sampling tissues of varying hardness. In the MAMMOTOME™ biopsy instrument, the cutter is rotated using a motor drive mounted in the instrument while the surgeon manually moves the cutter back and forth by a knob on the outside of the instrument. Thus, the surgeon is able, through tactile feedback, to determine whether the blade is effectively cutting tissue or if there is a problem, such as binding or stalling. The surgeon may then adjust the speed at which the blade is moved through the tissue, stop the blade, or back the blade away from the tissue. The device can also be used to collect multiple samples in numerous positions about its longitudinal axis, without removing the biopsy needle from the body. These features allow for substantial sampling of large lesions and complete removal of small ones. In the MAMMOTOME™, a vacuum chamber is attached alongside and fluidly connected to an elongated, hollow needle. The vacuum supplied through the vacuum chamber pulls tissue into the lateral receiving port of the hollow needle.

For breast biopsies, the devices described so far are most commonly used in combination with either X-ray or ultrasound imaging to locate suspicious tissue, although other imaging modalities such as magnetic resonance imaging are also available. When using, for example, the MAMMOTOME™ biopsy device with an X-ray stereotactic table, the biopsy device is attached to a movable, mechanical mounting arm. The patient lies face down on the table and the patient's breast is guided through an opening in the stereotactic table. Several X-ray images of the breast are taken from different angles to determine the location of the calcifications or lesions, which are to be removed from the breast. Next the mounting arm is manually repositioned so that the biopsy device is properly aligned with the breast. Then the mounting arm is manipulated to push the needle of the biopsy device into the breast until the tip of the needle is positioned alongside the tissue to be sampled. Additional X-ray images are then made to confirm that the port on the distal end of the needle is in the proper position to collect the desired tissue portions. The biopsy device is then used to retrieve one or more core samples of tissue. Additional X-ray images are taken to confirm the removal of the suspect tissue. Sometimes the biopsy device and mounting arm must be repositioned during the procedure so that the tip of the piercing element is in a new location in order to retrieve more tissue samples. As this brief description illustrates, there are many time consuming steps in getting the biopsy device properly positioned to retrieve the desired tissue. In addition, the accessibility of certain parts of the breast may be hindered by the degrees of freedom of the movement of the mounting arm. Also, the size of the stereotactic table and associated equipment precludes portability of the system. It is not possible, for example, to have a number of patients being prepared for the procedure in separate rooms of a clinic, if there is only one room set-up for doing the procedure. Having a portable system would allow the surgeon to go from room-to-room and perform the procedure, and thus allow more patients to be treated in a given time period at the clinic.

Biopsy devices are also used with other kinds of X-ray imaging systems such as those for which the patient is upright rather than lying down. The numerous steps described above for locating, confirming, and reconfirming using X-ray stereo "snapshots" are also necessary for the upright versions.

The MAMMOTOME™ biopsy instrument may also be used with real time handheld imaging devices such as ultrasound imaging devices. When using a biopsy instrument such as the MAMMOTOME™ with a handheld ultrasound imaging device, the surgeon gains the advantage of having real time imaging of the tissue of interest. Typically the ultrasound imaging device is held in one hand and pointed at the tissue being penetrated by the needle. In order to facilitate positioning and manipulation of both the biopsy instrument and the imaging device, it is normally necessary to attach the biopsy instrument to a mechanical, articulating arm which is designed to support the weight of the biopsy instrument. In addition, since axial movement of the cutter on the MAMMOTOME™ is actuated by hand, the biopsy device must be rigidly supported to allow the surgeon to actuate the cutter without moving the tip. Alternatively, an assistant may be used to help operate the controls for the biopsy device. It would, therefore, be advantageous to design a handheld core sampling biopsy instrument wherein the cutter of the instrument was moved using a motor drive which could be actuated by the touch of a switch. Further, since some of the electrical and vacuum controls are not on the MAMMOTOME™ biopsy instrument itself, the biopsy instrument must be rigidly supported or the surgeon must have an assistant to actuate the controls. It would, therefore, be further advantageous if the electrical and vacuum controls for the biopsy device were positioned in relatively close proximity either on the instrument or, for example, on an associated generator. Automating axial movement of the cutter will, to some extent, eliminate the tactile feedback that the surgeon gets from moving the cutter blade manually. It would, therefore, be advantageous to provide a method of automatically measuring and controlling the axial movement of the cutter, which could be utilized to, for example, prevent the cutter from advancing when the port is blocked.

In recent years several patents have issued describing handheld, motorized devices for the extraction of tissue from the body. Many of these devices are for arthroscopic surgery and are not intended for retrieving biopsy core samples of tissue for pathological analysis. The motors are for rotationally driving the cutting/milling end effectors, but not for advancing the end effectors into the tissue. Examples of arthroscopic, handheld, motorized devices include the following U.S. Pat. Nos. 4,995,877; 4,705,038; 5,192,292; 5,112,299; 5,437,630; 5,690,660; and 5,320,635.

In U.S. Pat. No. 4,940,061 issued to Terwilliger, et al, on Jul. 10, 1990, a core sampling, handheld biopsy device incorporating a battery powered motor for driving a means to penetrate and sever tissue is described. The motor axially drives a cutter to advance the cutter into tissue, thus eliminating the noise and jerking associated with mechanical stops of the spring-actuated devices. This significantly adds to the comfort of both the patient and the surgeon. However, the device does not incorporate a vacuum source for obtaining the tissue portion. As described in Burbank, et al., '822 and '333, the vacuum greatly facilitates the capturing of a complete tissue portion within the distal end port on the piercing element. Capturing more tissue with each sample reduces the number of samples required, and increases the likelihood of obtaining the diseased tissue. The Terwilliger device in '061 also does not address how to minimize leakage and spilling of the high volume of fluids present in biopsy procedures.

The surgeon may prefer to use an X-ray imaging system for some patients, and an ultrasound imager for others. In such situations, it would be desirable to use a biopsy instrument that is adaptable to both kinds of imaging systems.

Such an instrument could be used as a handheld instrument or also as an instrument mounted onto the arm of an X-ray stereotactic table, depending on the situation.

It is therefore desirable to provide a more versatile and "patient friendly" biopsy device than what is currently available. The device should be particularly adapted for use without mounting to an X-ray stereotactic table. It should be a lightweight, maneuverable, handheld device, so that the surgeon may have the option to perform the biopsy procedure in combination with an ultrasound imaging device. It is desirable that the device be easily transported from room-to-room so that several patients may be prepared for the surgical procedure concurrently, thus allowing more patients to be treated in a given time period, and potentially reducing the overall cost of the surgical procedure. In addition, it is desirable to perform a biopsy with fewer steps in order to decrease the overall time of the procedure. This would be achievable by eliminating the need to set-up and operate the X-ray stereotactic table. The combination of these factors could allow the surgical procedure to be more widely available to patients than it is currently.

It is also desirable to provide a handheld biopsy device that may be held parallel to the chest wall of the patient, so that suspect tissue masses close to the chest wall can be easily sampled. It is desirable that the surgeon be able to easily steer the penetrating tip of the handheld device towards the desired tissue to be sampled. It is further desired that the surgeon have tactile feedback as the tissue is probed by the penetrating tip of the device, to provide the surgeon with clues regarding the disease state of the tissue encountered. It is also desirable that the biopsy device be "patient friendly" by not having noisy or jerky mechanical actuations during the procedure, and by not having to be used with large machines such as an X-ray stereotactic table.

SUMMARY OF THE INVENTION

The present invention overcomes problems associated with using a biopsy instrument that may be used only when mounted to an X-ray stereotactic system.

In the preferred embodiment, the present invention is a handheld biopsy device that may be used in combination with another handheld imaging device such as an ultrasound imaging device. The present invention provides a biopsy instrument for the collection of at least one soft tissue sample from a surgical patient. The present invention provides a biopsy instrument having a handpiece that is independently manipulatable by hand movement of the instrument toward and away from the patient. The present invention incorporates an elongated needle extending from the distal end of the hand piece and having a needle lumen therein and a sharpened distal end for entering tissue when the hand piece is moved by hand toward the surgical patient so as to cause the sharpened distal end to penetrate tissue.

The present invention also includes an elongated cutter with a central lumen therethrough. The cutter is disposed coaxially and slidably relative to the needle. The cutter has a cutting blade on the distal end for cutting the portion of tissue protruding into the specimen receiving port of the needle when the cutter slides distally past the port. A portion of the cut tissue is then deposited within the cutter lumen proximal to the cutting blade.

The present invention includes a cutter rotational transmission contained within the hand piece and operationally connected to the elongated cutter. When the cutter rotational transmission is actuated, die cutter is rotated about its longitudinal axis.

The present invention further includes a cutter axial transmission contained within the hand piece and operationally connected to the elongated cutter. When the cutter axial transmission is actuated, the cutter is slid in an axial direction relative to the needle. It is slid in the distal axial direction to cut a portion of tissue protruding into the port. It is slid in the proximal axial direction to retrieve the cut portion of tissue from the biopsy instrument.

The biopsy device also has a power transmission source that is operationally engageable with the cutter rotational transmission for rotation of the cutter. In the preferred embodiment, the power transmission source is also operationally engageable with the cutter axial transmission for the longitudinal movement of the cutter. A first electric motor is operationally engaged to the cutter rotational transmission by a first flexible, rotatable shaft. A second electric motor is operationally engaged to the cutter axial transmission by a second flexible, rotatable shaft. The hand piece also includes a holster. The distal ends of the first and second rotatable shafts are rotatably mounted in the holster so that the first and second shafts are operationally engaged, respectively, to the cutter rotational transmission and the cutter axial transmission inside the hand piece.

In the preferred embodiment of the present invention, a specimen collection tube is disposed in the cutter lumen of the cutter. By activating the axial transmission source, the cutter is slid fully distal to cut a portion of tissue protruding in the port. Continued activation of the axial transmission source advances the specimen push rod distally forcing it around a 180 degree bend in the tip of the needle and back into the distal end of the cutter. This action results in the specimen push rod pushing tissue specimens proximally within the cutter thereby creating space within the cutter for the next specimen. By reversing the axial transmission source, the specimen push rod retracts distally out of the tube followed by the cutter retracting proximally exposing the port for the next tissue sample. The proximal end of the tissue remover is connected to a first vacuum tube that is connected by a first connector to a fluid collection system. The fluidic contents of the cutter lumen are transported to the fluid collection system when the vacuum is actuated. A strainer on the distal end of the remover is provided to block the tissue portion from entering the remover.

Also in the preferred embodiment, the proximal end of the needle lumen is connected by a second vacuum tube that is connected by a second connector to the fluid collection system. The fluidic contents of the needle lumen also are transported to the fluid collection system when the vacuum of the system is actuated.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 4 presents a top view of the biopsy device illustrated in FIG. 1, having the top cover removed, showing the internal mechanism in its initial starting configuration.

FIG. 4A presents a cross-section taken along line 4A-4A in FIG. 4.

FIG. 5 presents a cross-sectional view taken along line 5-5 in FIG. 4.

FIG. 21 presents a top view of the biopsy device illustrated in FIG. 18, having the top cover removed, showing the internal mechanism in its initial starting configuration.

FIG. 21A presents a cross-section taken along line 21A-21A in FIG. 21.

FIG. 22 presents a cross-sectional view taken along line 22-22 in FIG. 21.

FIG. 25 presents a top view of the biopsy device, similar to FIG. 21, showing the internal mechanism with the cutter at the distal end of the insertion needle.

FIG. 26 presents a cross-sectional view taken along line 26-26 in FIG. 25.

FIG. 27 presents a cross-sectional view, similar to FIG. 24, of the distal end of the insertion needle illustrating a tissue sample within the cutter after having been cut.

FIG. 28 presents a top view of the biopsy device, similar to FIGS. 21 and 25, showing the internal mechanism of the biopsy instrument with the cutter and the push rod at their extended distal configuration.

FIG. 29 presents a cross-sectional view, of the biopsy instrument, similar to FIG. 26, showing the internal mechanism of the biopsy instrument with the cutter and the push rod at their extended distal configuration.

FIG. 30 presents a cross-sectional view, similar to FIGS. 24 and 27, showing the cut tissue sample having been pushed into the cutter by the flexible push rod.

DETAILED DESCRIPTION OF THE INVENTION

Preferred Embodiment—Structure

Figure 1:
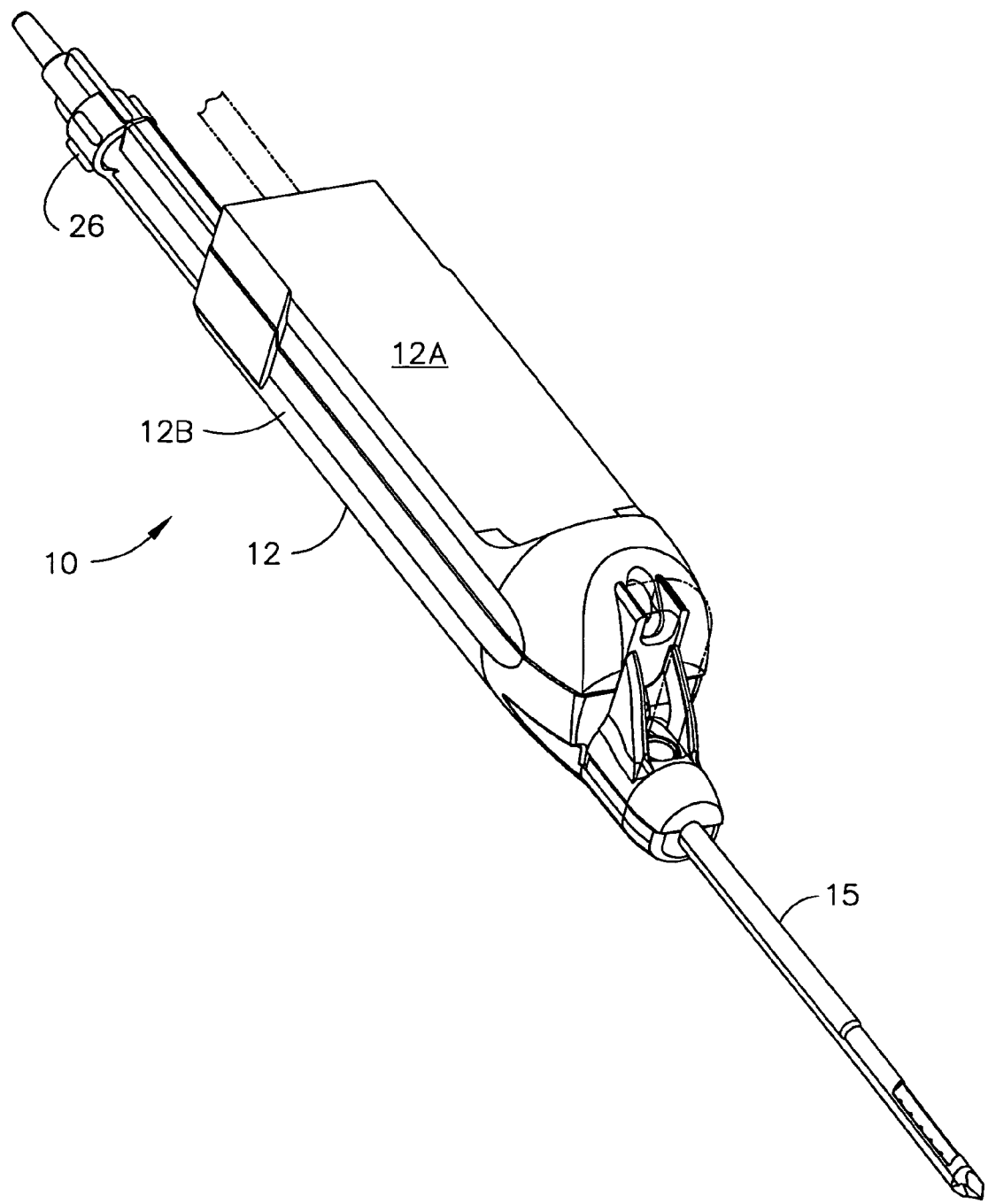
FIG. 1 presents a perspective view of a biopsy device embodying the present invention.
Figure 2:
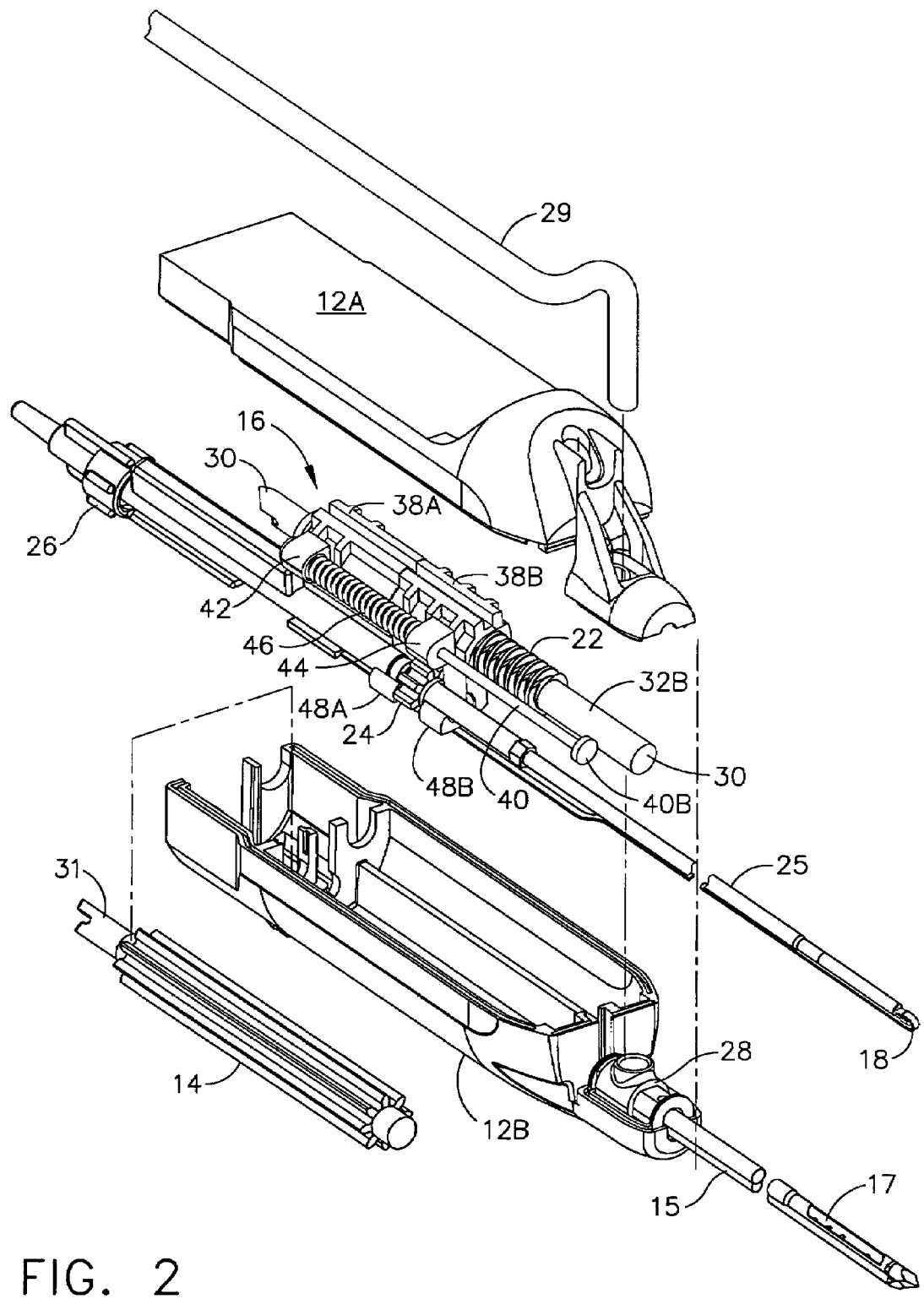
FIG. 2 presents an exploded perspective of the biopsy device illustrated in FIG. 1.
Figure 3:
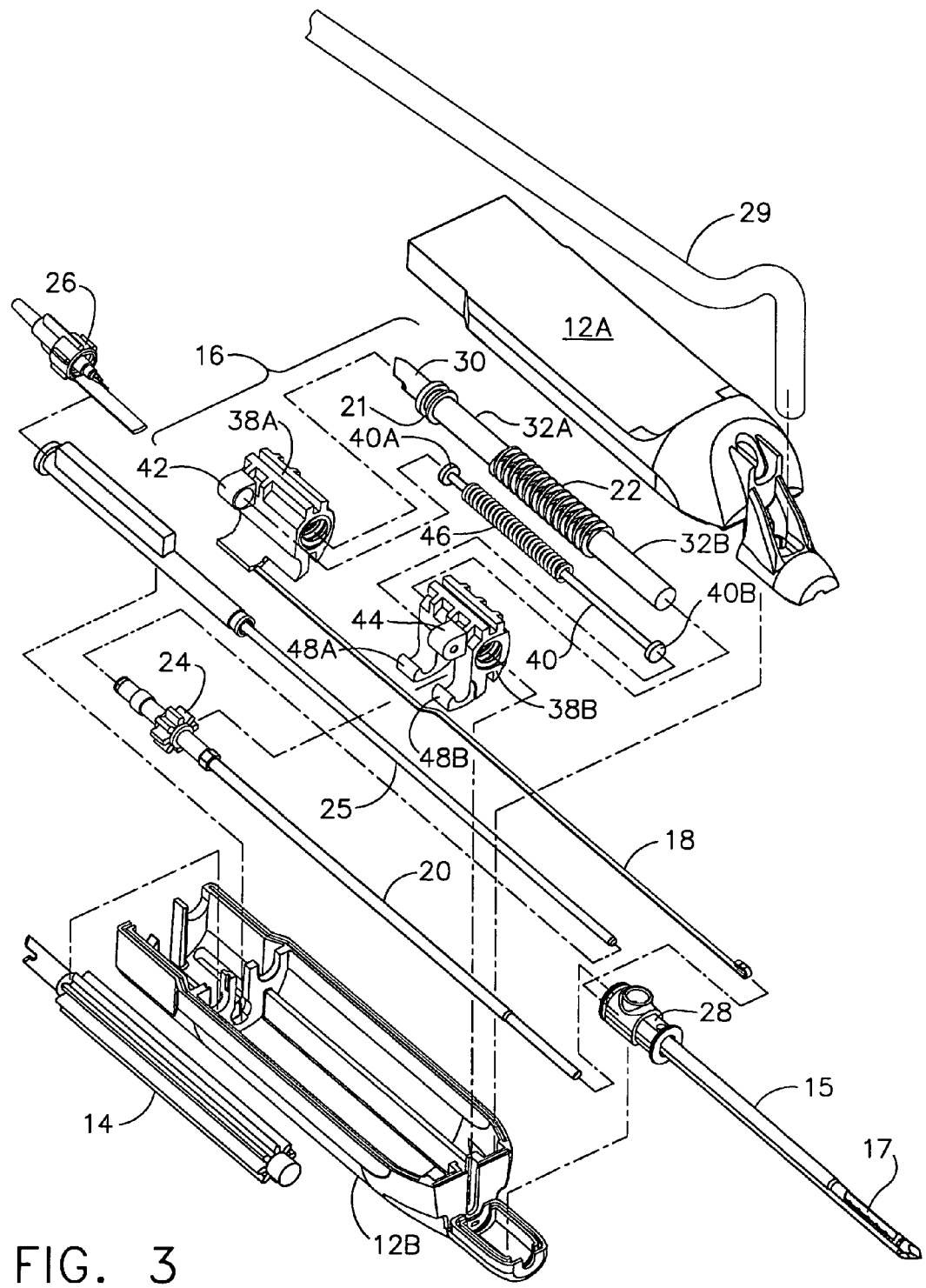
FIG. 3 presents an exploded perspective, similar to that of FIG. 2, wherein the component parts of the specimen push rod mechanism is further illustrated as an additional exploded pictorial.
Figure 3A:
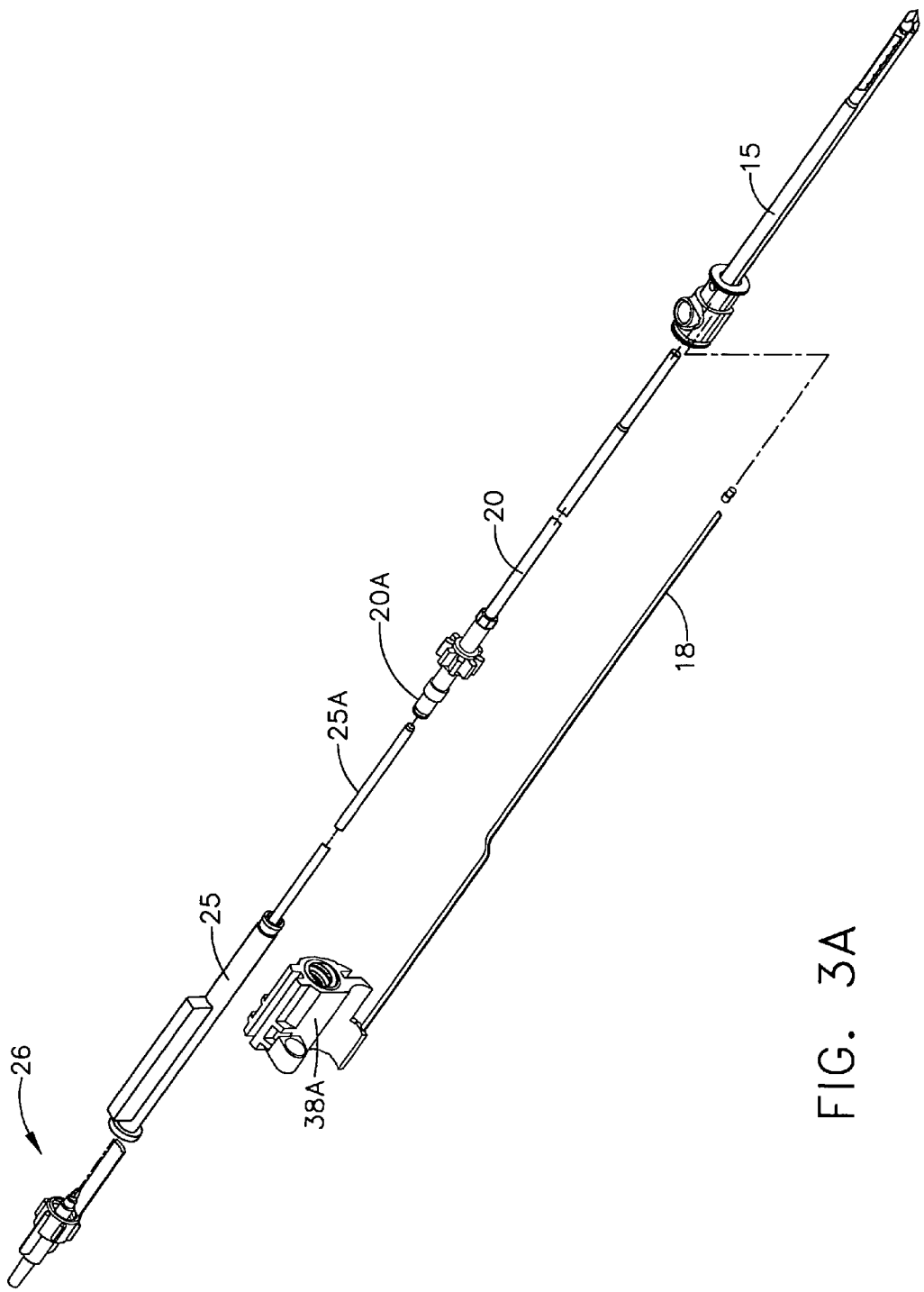
FIG. 3A presents a pictorial view of the specimen collection tube and cutter subassembly along with the specimen push rod.

Referring to FIGS. 1 through 3A, a hand held biopsy instrument 10, embodying the present invention, is illustrated. Biopsy instrument 10 comprises an outer housing 12 comprising a top and bottom shell 12A and 12B respectively. Extending distally outward from bottom shell 12B is biopsy needle 15 the function of which will become apparent below. Contained within housing 12 is drive mechanism 16 for operating the specimen cutter 20 and specimen collector tube 25 subassembly, along with specimen push rod 18 as illustrated in FIG. 3A.

Specimen collection tube 25 is coaxially positioned within cutter 20 that in turn is coaxially positioned within the upper lumen 13 of the biopsy needle 15 as illustrated in FIGS. 3, 3A, and 4A. Push rod 18 is positioned within the lower lumen 19 within biopsy needle 15 as indicated in FIGS. 3, 3A, and 4A. A vacuum port connector with knockout pin 26, fluidly attached to a vacuum source (not shown), is attached to the proximal end of specimen collection tube 25, the operation and function of which will be further explained below. A vacuum port 28, receiving therein vacuum source tube 29, is provided at the proximal end of needle 15 for providing a vacuum within the lower lumen 19 of biopsy needle 15. The purpose of providing a vacuum within needle 15 will be further explained below.

Figure 6:
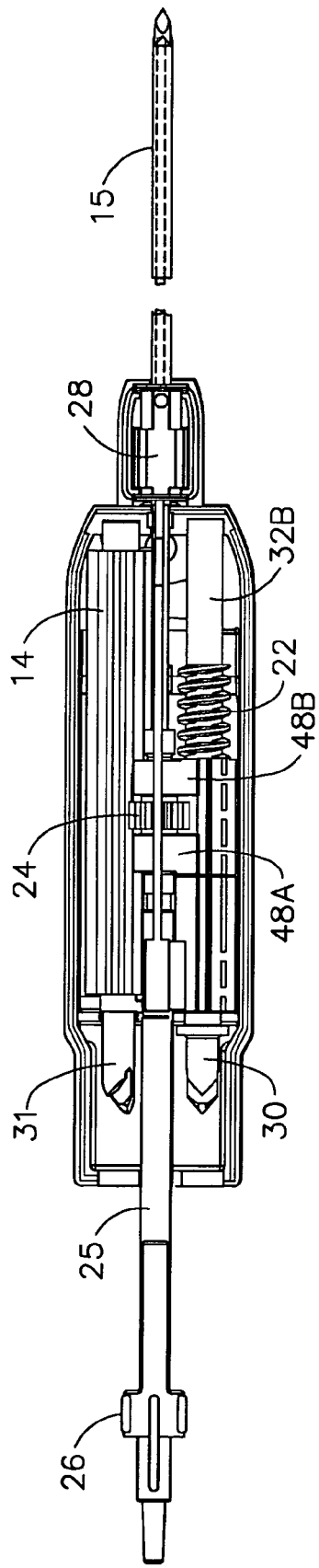
FIG. 6 presents a bottom view of the biopsy device illustrated in FIG. 1, having its bottom cover removed, showing the internal mechanism in its initial starting configuration.

Also contained within housing 12 is elongated drive gear 14 engaging cutter drive gear 24, as shown in FIG. 6, for rotating cutter 20. Operation of drive mechanism 16 is provided by separately powered worm gear 22.

As best illustrated in FIG. 3, the worm gear threaded portion 22 of drive shaft 30 only extends over approximately the middle third of drive shaft 30; non threaded portions 32A and 32B are provided on the proximal and distal ends of drive shaft 30 respectively, the function of which is further explained below. Positioned upon drive shaft 30 are proximal and distal drive blocks 38A and 38B. Elongated rod 40 slidingly extends through boss 44 on drive block 38B and boss 42 of drive block 38A. End stops 40A and 40B is provided at the distal ends of rod 40, the function of which will be further described below. A compression spring 46 is axially positioned upon rod 40 between boss 42 and 44 of drive blocks 38A and 38B, as best illustrated in FIG. 2, providing an axial biasing force therebetween.

When assembled in the biopsy instrument's starting or initial configuration, as illustrated in FIG. 2, the cutter drive mechanism 16 comprises drive blocks 38A and 38B positioned upon worm gear 22 with block 38A at the far proximal end and block 38B adjacent thereto. In this configuration, block 38A rests upon the non-threaded portion 32A of drive shaft 30 and block 38B is threadingly engaged with worm gear 22. Compression spring 46 is fully compressed between bosses 42 and 44 thereby providing a biasing force tending to separate drive blocks 38A and 38B. However since drive block 38B is threadingly engaged with worm gear 22 and cannot move and block 38A is being forced against collar 21 at the proximal end of drive shaft 30 the two drive blocks cannot separate.

Coaxially positioned within cutter 20 is collection tube 25, as indicated in FIGS. 3 and 4A. Collection tube 25 has an engagement feature 25A that spans over a lip feature 20A on the proxial end of cutter 20. The engagement feature 25A enables the collection tube 25 to advance and retract in unison with the cutter 20, but as the cutter rotates it allows the collection tube 25 to not rotate. The subassembly comprising the cutter and collection tube is supported by journals 48A and 48B, on block 38B, such that cutter drive gear 24 lies therebetween, as illustrated in FIG. 2. Thus axial movement of drive block 38B upon worm gear 22 also causes axial movement of the subassembly comprising the cutter and the collection tube. Cutter drive gear 24 remains engaged with elongated drive gear 14 as cutter drive gear 24 advances axially toward the distal end. The cutter and collection tube, as a subassembly, is coaxially positioned within needle 15 along with and parallel to the specimen push rod 18 as indicated in FIGS. 3 and 4A. Specimen push rod 18 is affixed, at its proximal end, to drive block 38A as illustrated in FIG. 3. Thus as drive block 38A axially advances push rod 18 also advances. Attached to the proximal end of collection tube 25 is vacuum port connector with knockout pin 26.

Preferred Embodiment—Operation

FIGS. 4, 5, and 6 illustrate the positioning of elements prior to taking a tissue sample. Drive blocks 38A and 38B are positioned at their far most proximal location as best illustrated in FIGS. 4 and 5. In this position the cutter/specimen collection tube subassembly along with the specimen push rod are also positioned at their far most proximal location.

Figure 7:
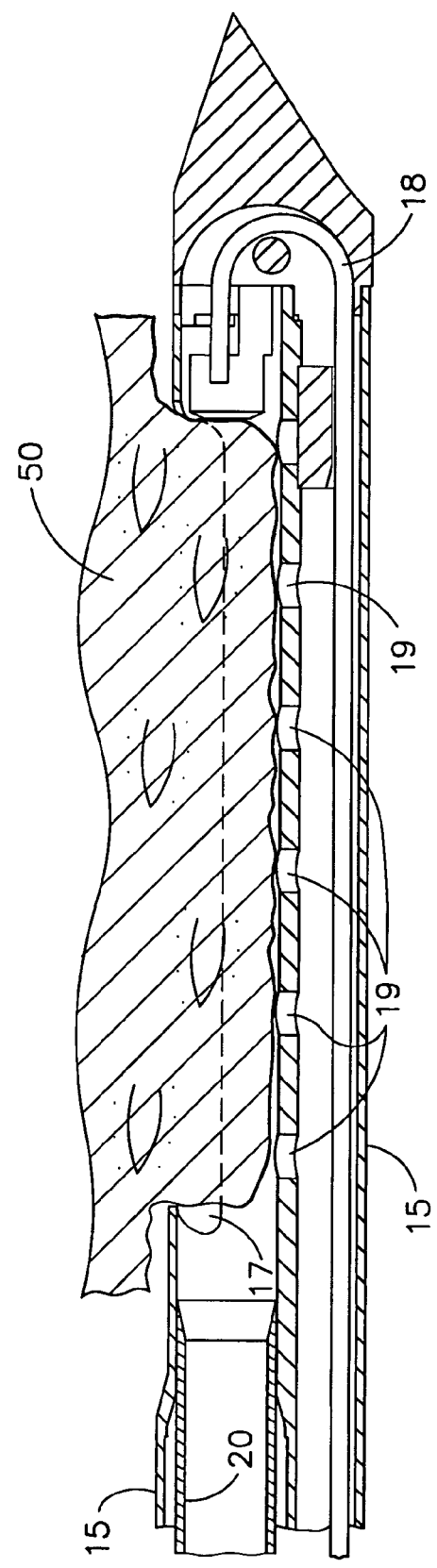
FIG. 7 presents a cross-sectional view of the distal end of the insertion needle illustrating tissue within the specimen sampling recess prior to being sampled.
Figure 8:
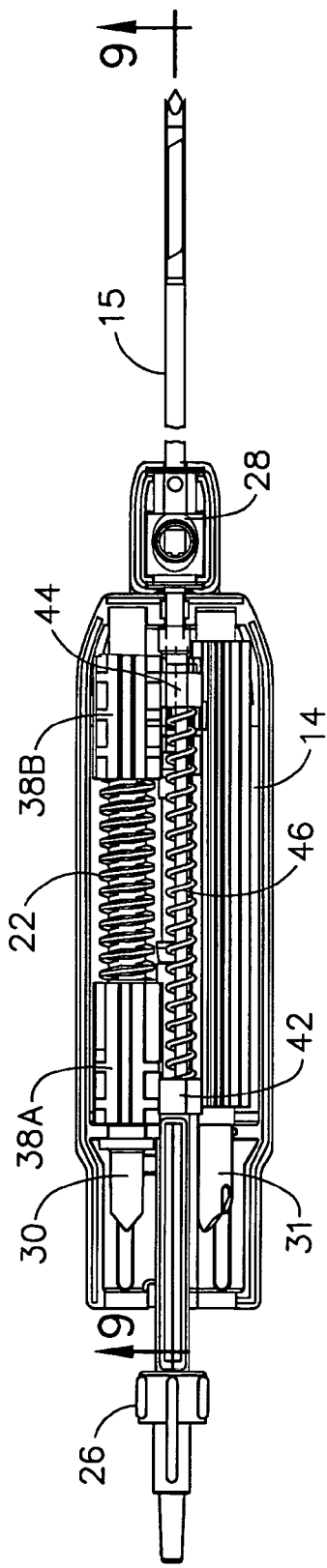
FIG. 8 presents a top view of the biopsy device, similar to FIG. 4, showing the internal mechanism with the cutter at the distal end of the insertion needle.
Figure 10:
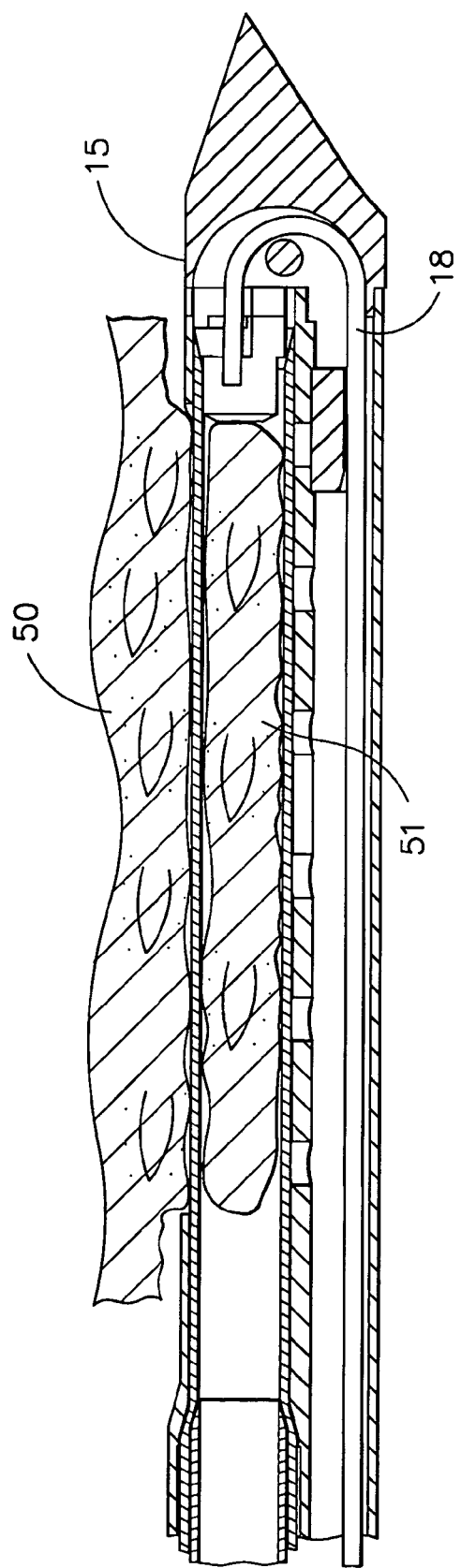
FIG. 10 presents a cross-sectional view, similar to FIG. 7, of the distal end of the insertion needle illustrating a tissue sample within the specimen sampling recess after having been cut.

To take a tissue specimen, needle 15 is inserted into the tissue to be sampled as illustrated in FIG. 7. A vacuum, supplied from vacuum 29 through port 28 is provided inside needle 15. Tissue 50 is drawn into specimen port by action of the applied vacuum through orifices 19 in specimen needle 15. Drive shaft 31 is rotated thereby rotating cutter 20 through the engagement of cutter drive gear and drive gear 14. Simultaneously drive shaft 30 is rotated, rotating worm gear 22, whereby drive block 38B advances toward the distal end of the biopsy instrument 10. As drive gear 38B advances rotating cutter 20 also advances until drive block 38B runs off worm gear 22 and onto the non-threaded portion 32B of drive shaft 30. When drive block 38B reaches its distal end, as illustrated in FIG. 8, cutter 20 will have cut and encapsulated a sample portion of tissue 51 as shown in FIG. 10.

Figure 9:
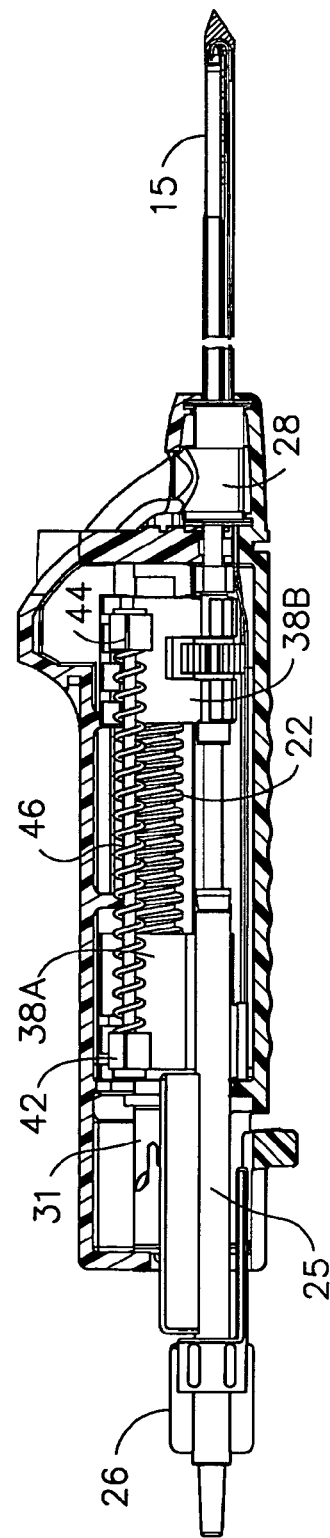
FIG. 9 presents a cross-sectional view taken along line 9-9 in FIG. 8.

As drive block 38B advances onto the non-threaded portion 32B, of drive shaft 30, end stop 40B on elongated rod 40 has been advanced by the boss 44 of drive block 38B. As elongated rod 40 is advanced, end stop 40A contacts boss 42 of drive block 38A, see FIGS. 8 and 9, thereby drawing drive block 38A onto worm gear 22. As drive block 38A advances upon worm gear 22 coil spring 46 is once again placed into a compression mode thereby continuing to bias drive block 38A and 38B apart. Also as drive block 38A advances, specimen push rod 18 also advances, within lower lumen 19. And as a result of the internal curvature of the needle tip, as the specimen push rod is advanced distally within the lower lumen 19 it is deflected around the 180 degree curvature and back into the upper lumen. Thereby pushing specimen 51 in the proximal direction and into specimen collection tube 25 as illustrated in FIGS. 12 and 13.

Figure 11:
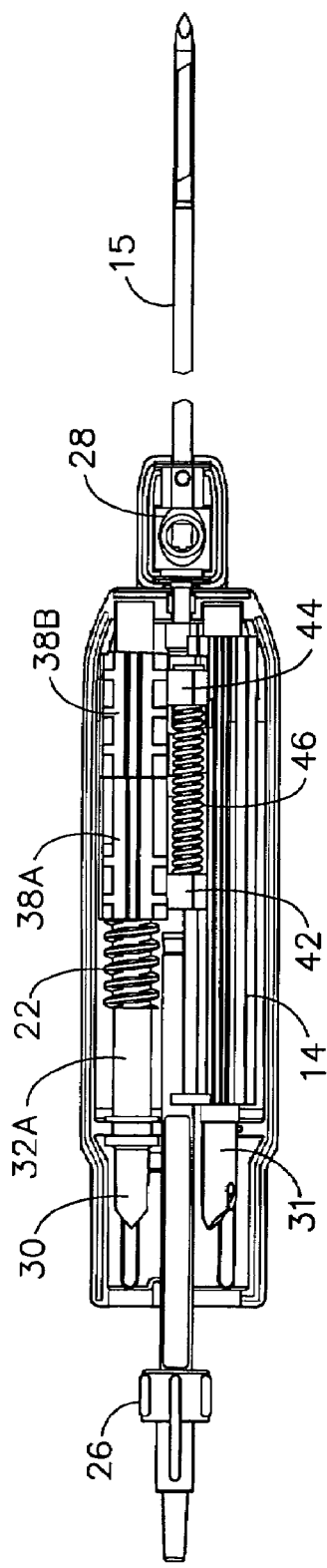
FIG. 11 presents a top view of the biopsy device, similar to FIGS. 4 and 8, showing the internal mechanism of the biopsy instrument with the cutter and the push rod at their extended distal configuration.
Figure 12:
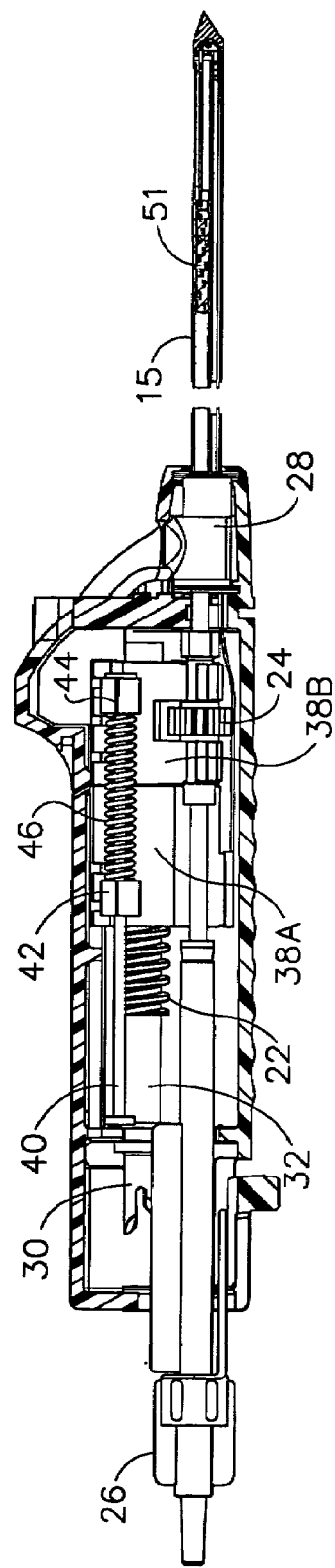
FIG. 12 presents a cross-sectional view, of the biopsy instrument, similar to FIG. 9, showing the internal mechanism of the biopsy instrument with the cutter and the push rod at their extended distal configuration.
Figure 13:
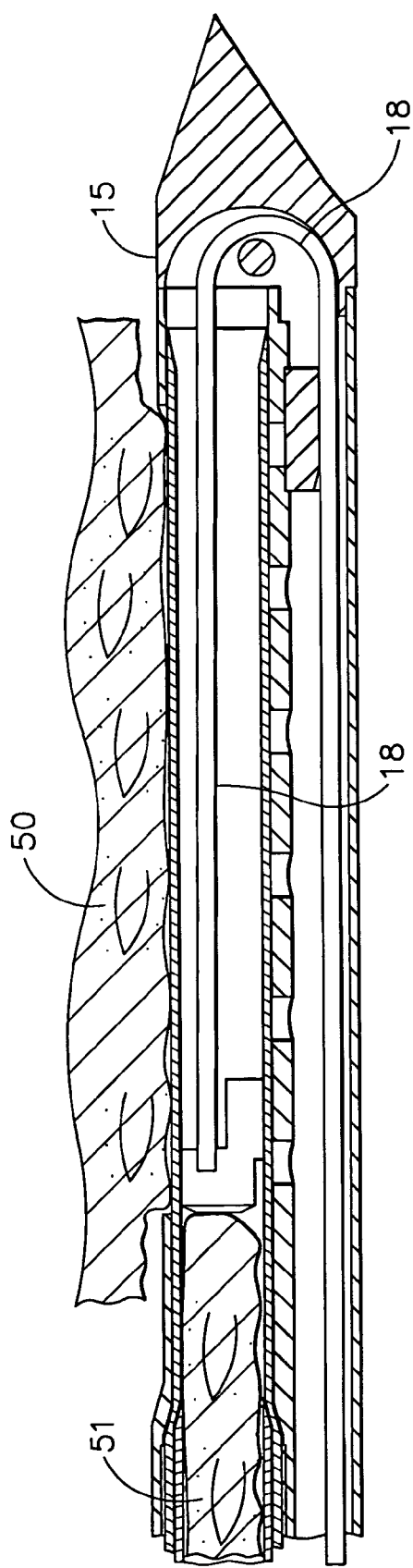
FIG. 13 presents a cross-sectional view, similar to FIGS. 7 and 10, showing the cut tissue sample having been pushed into the sampling tube by the flexible push rod.

Once drive block 38A reaches drive block 38B, as illustrated in FIGS. 11 and 12, the sampling operation is ended. Drive shaft 30 is reversed whereby drive block 38A engages with the threads on worm gear 22 by the biasing action of the compression spring 46. Drive block 38A is returned to its starting position as illustrated in FIG. 8 thereby returning specimen push rod 18 to its starting position. As drive block 38A retracts onto the non-threaded portion 32A, of drive shaft 30, elongated rod 40 has been retracted by the drive block 38A. As elongated rod 40 is retracted, end stop 40B contacts boss 44 of drive block 38B, see FIGS. 8 and 9, thereby drawing drive block 38B onto worm gear 22. As drive block 38B reverses direction, the cutter 20 also retracts.

Although it may not be necessary, it is preferred to provide a separate vacuum within specimen tube 25, through vacuum port connector 80 with knockout pin 26 to prevent specimen 51 from moving toward the distal end of the cutter 20 under the influence of the vacuum provided within biopsy needle 15, as the specimen push rod is retracted.

Figure 14:
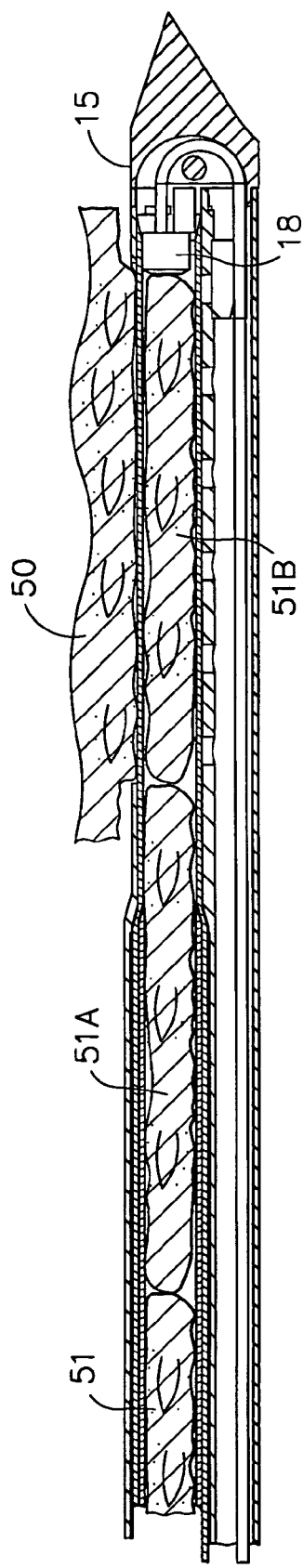
FIG. 14 presents a cross-sectional view showing multiple cut tissue samples having been pushed into the sampling tube by the flexible push rod.
Figure 15:
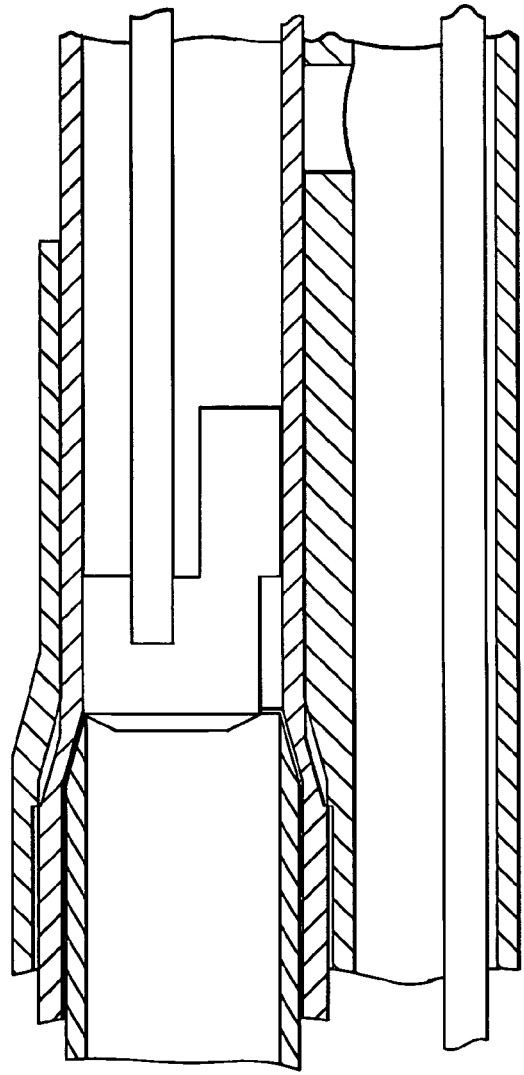
FIG. 15 presents an enlarged view of the area circled in FIG. 13.

After all elements have been returned to their original start configuration, the operation may be repeated to take a second specimen. By this operation successive, multiple specimens 51, 51A, and 51B, may be taken and stored in the order taken as illustrated in FIG. 14.

Figure 17:
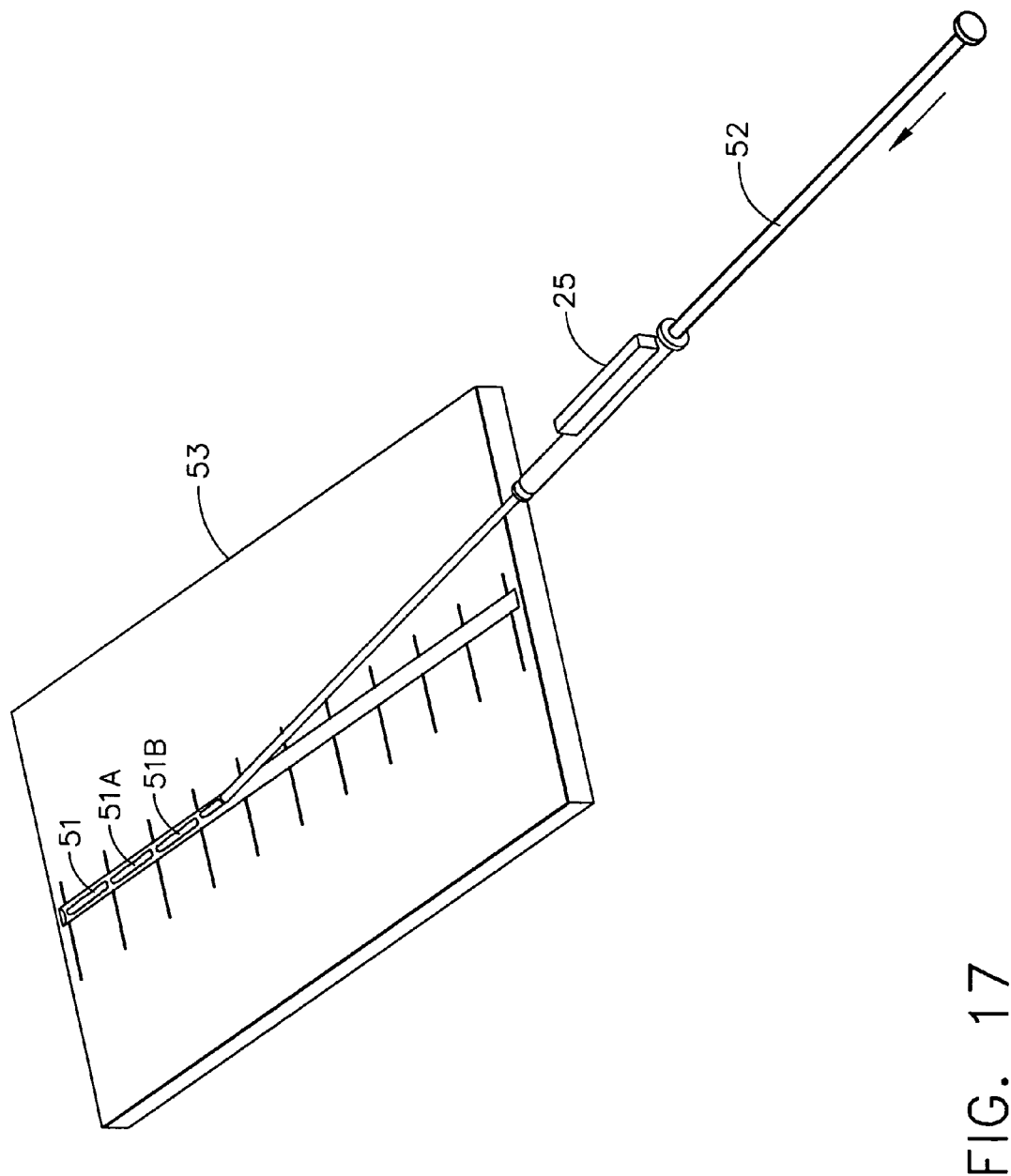
FIG. 17 presents a pictorial illustration of a specimen board receiving a series of collected specimens discharged, from the sampling tube, in the order that they were taken.

After the specimens have been collected within collection tube 25, collection tube 25 may be removed from the biopsy instrument and, using a simple push rod 52 the specimens may be placed upon a specimen holding tray 53 as illustrated in FIG. 17.

Figure 16:
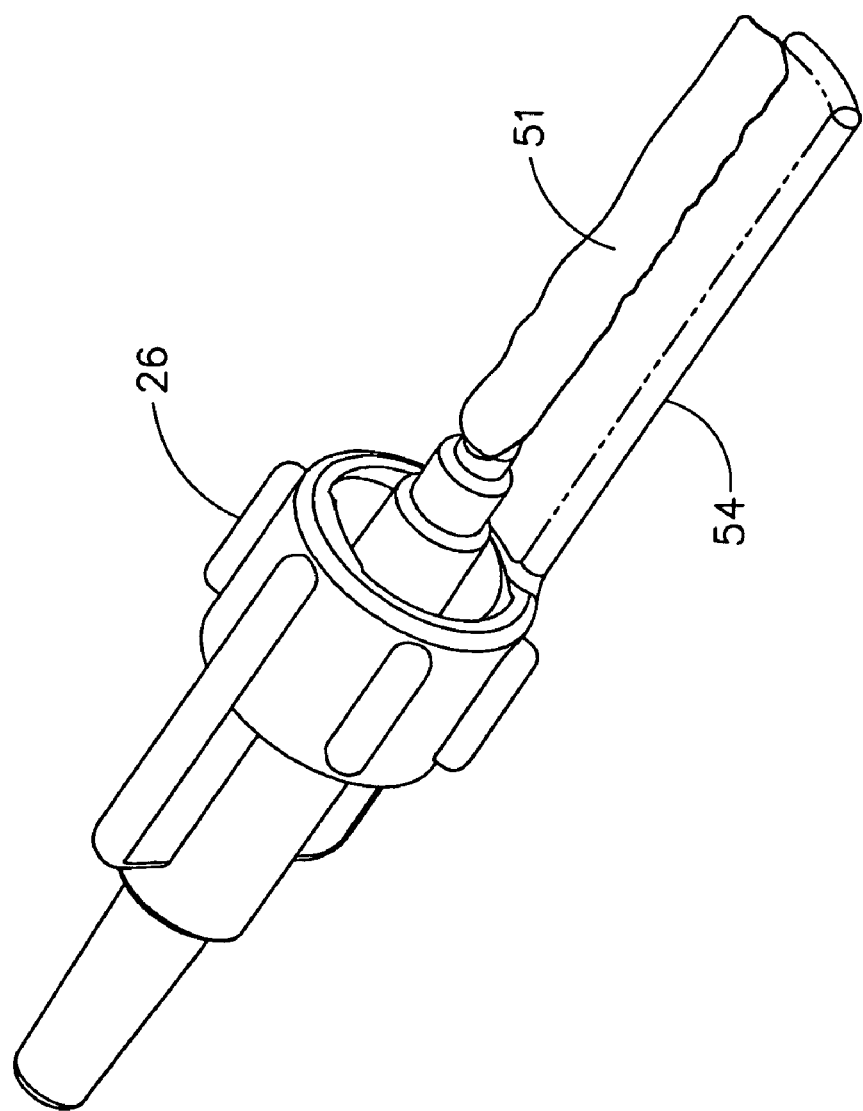
FIG. 16 presents a pictorial view of the vacuum port connector with integral knockout pin.

In the event that it is desired that each specimen be removed as it is sampled, the single specimen 51 may be drawn by vacuum to vacuum port connector 26 with integral knockout pin and withdraw upon an integral specimen catching tray 54 extending from vacuum port connector 26 with integral knockout pin as illustrated in FIG. 16.

Alternate Embodiment—Structure

Figure 18:
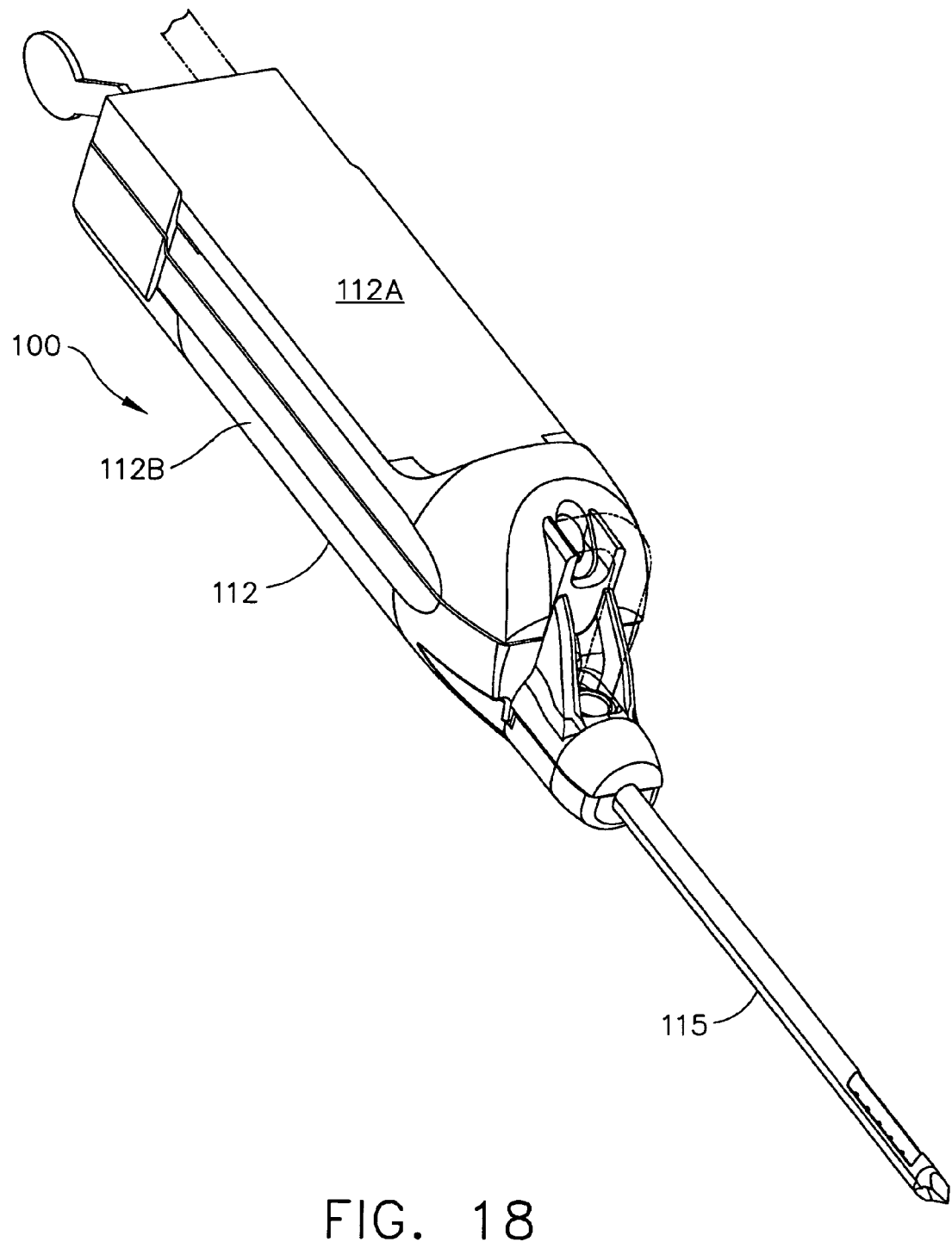
FIG. 18 a perspective view of an alternate embodiment of a biopsy device embodying the present invention.
Figure 19:
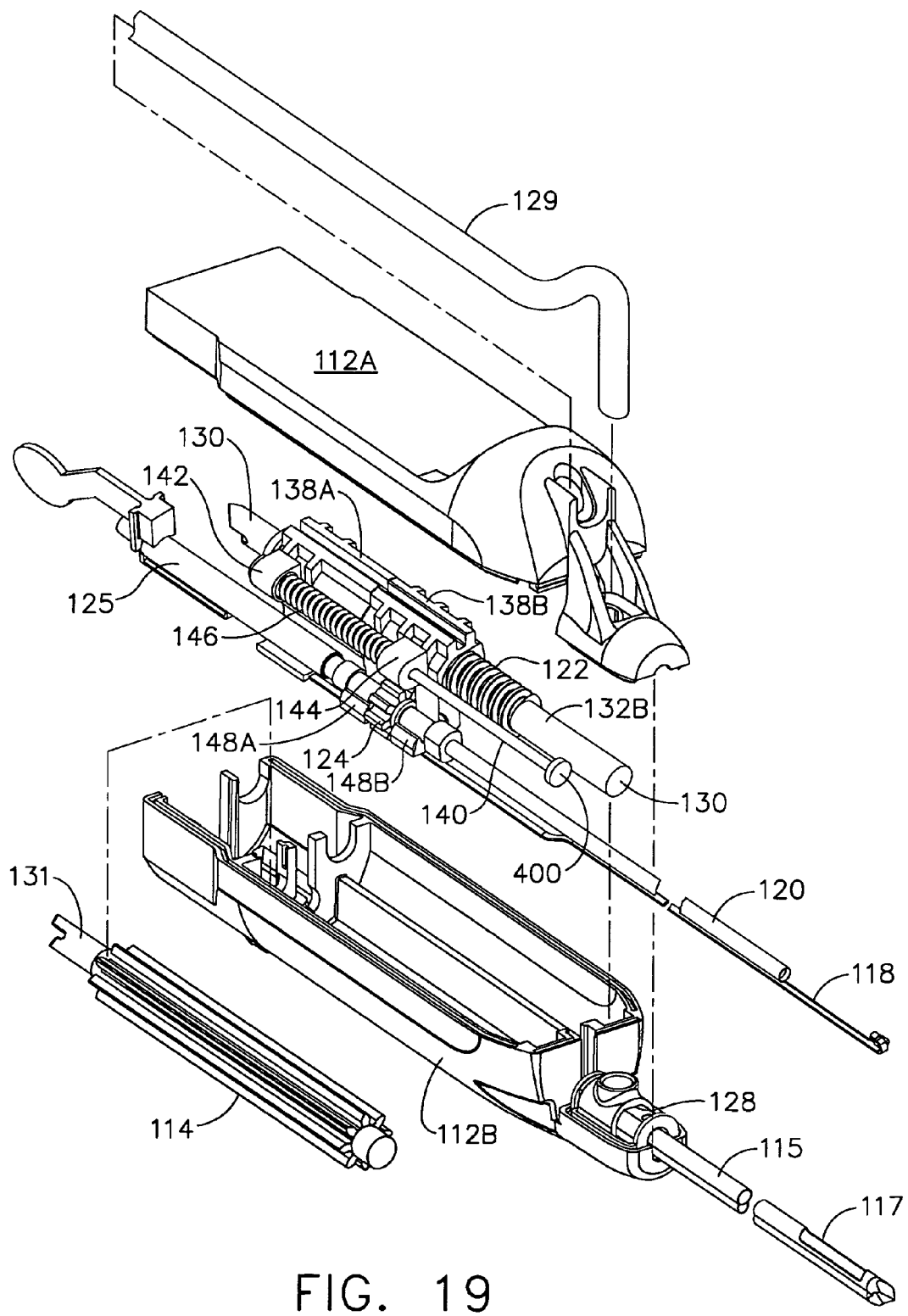
FIG. 19 presents an exploded perspective of the biopsy device illustrated in FIG. 18.
Figure 20:
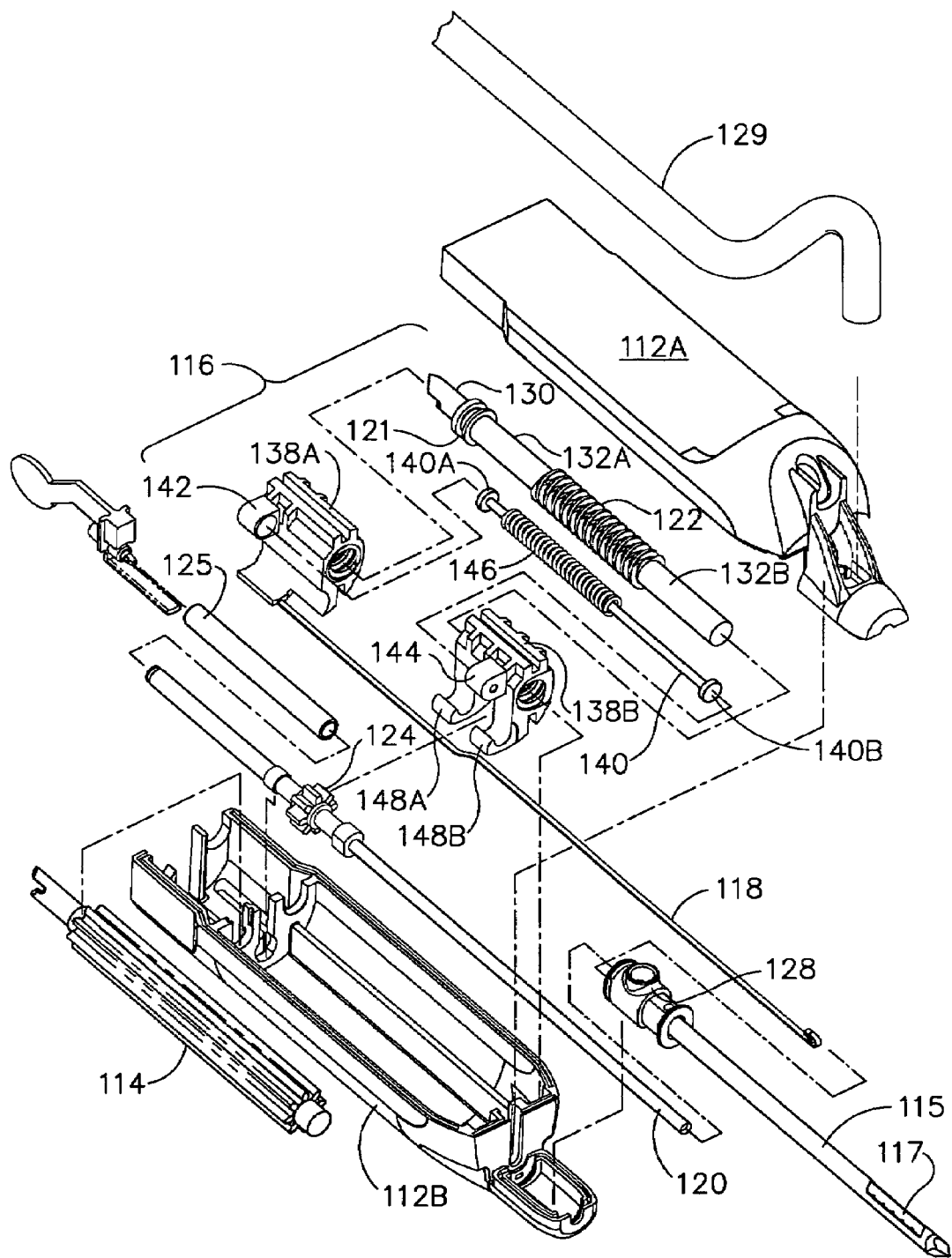
FIG. 20 presents an exploded perspective, similar to that of FIG. 19, wherein the component parts of the specimen push rod mechanism is further illustrated as an additional exploded pictorial.
Figure 20A:
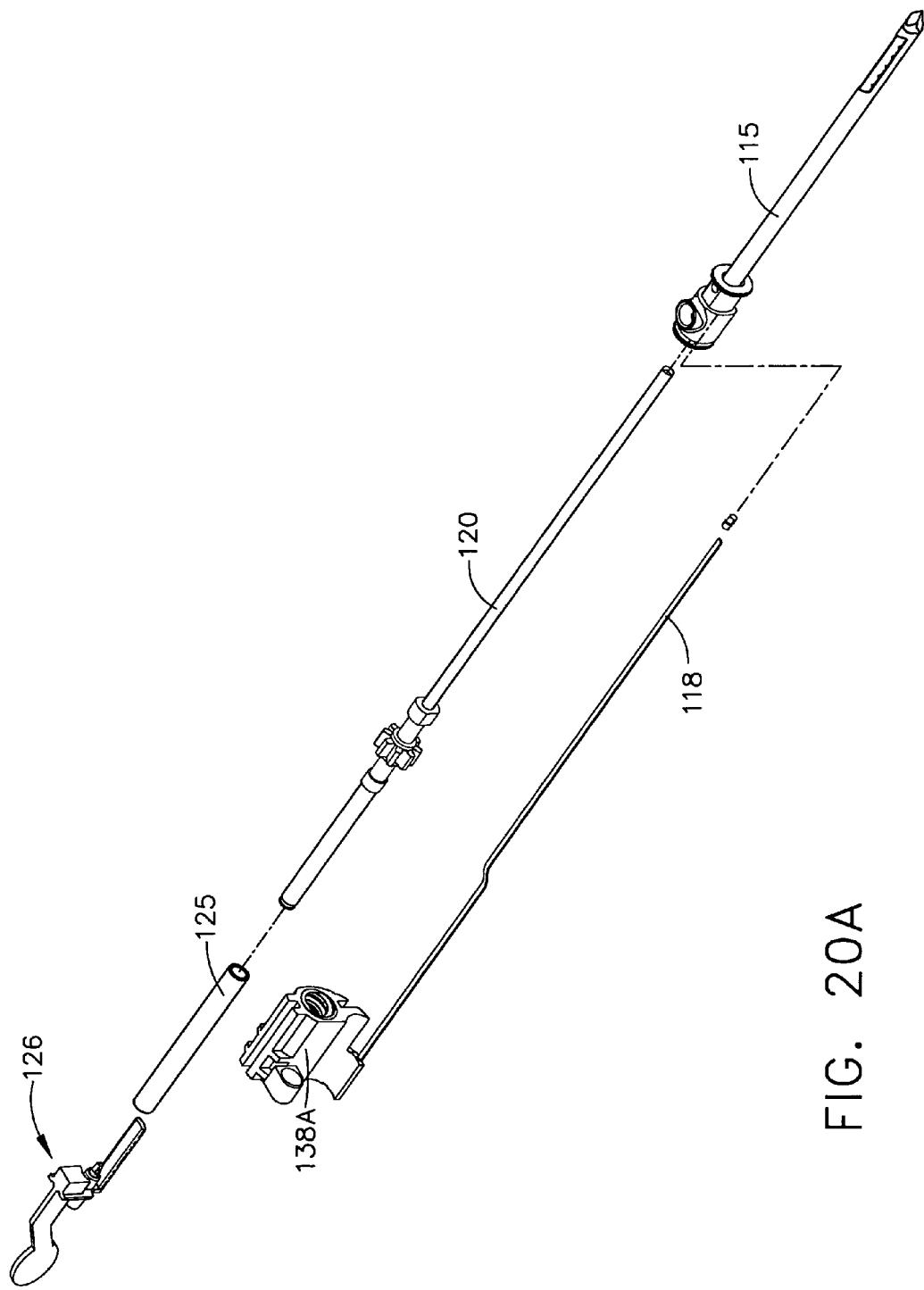
FIG. 20A presents a pictorial view of the cutter sleeve and cutter subassembly along with the specimen push rod.

Referring to FIGS. 18 through 20 a hand held biopsy instrument 100, embodying the present invention, is illustrated. Biopsy instrument 100 comprises an outer housing 112 having a top and bottom shell 112A and 112B, respectively. Extending distally outward from bottom shell 112B is biopsy insertion needle 115 the function of which will become apparent below. Contained within housing 112 is drive mechanism 116 for advancement of hollow tube cutter 120 and specimen push rod 118. Cutter 120 is coaxially positioned within the upper lumen 113 of the biopsy needle 115 as indicated in FIGS. 20 and 21A Push rod 118 is located within lower lumen 119 within biopsy needle 115 as indicated in FIGS. 20, 20A, and 21A. In this embodiment, a cutter sleeve 125 is located at the proxial end of the cutter to allow the cutter 120 to coaxially slide within the stationary cutter sleeve 125. A vacuum port connector with knockout pin 126, fluidly attached to a vacuum source (not shown), is attached to the proximal end of cutter sleeve 125, the operation and function of which will be further explained below. A vacuum port 128, receiving therein vacuum source tube 129, is provided at the proximal end of needle 115 for providing a vacuum within lower lumen 119 of biopsy needle 115. The purpose of providing a vacuum within needle 115 will be further explained below.

Figure 23:
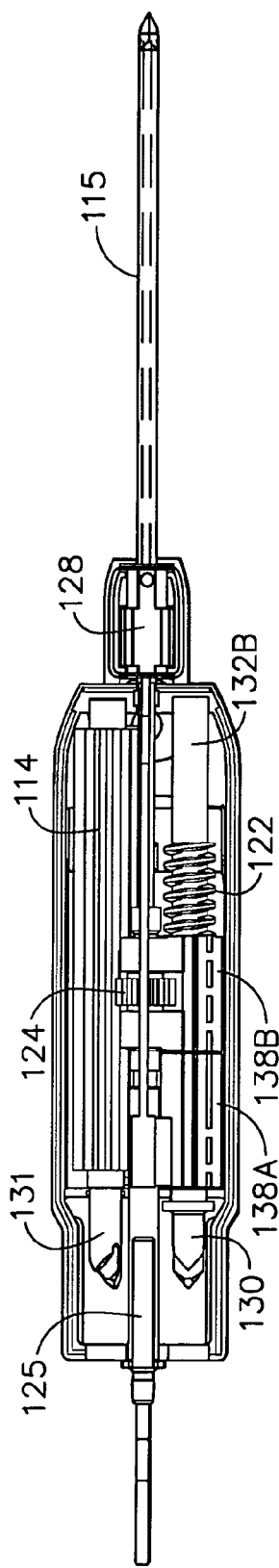
FIG. 23 presents a bottom view of the biopsy device illustrated in FIG. 18, having its bottom cover removed, showing the internal mechanism in its initial starting configuration.

Also contained within housing 112 is elongated drive gear 114 engaging cutter drive gear 124, as shown in FIG. 23, for rotating cutter 120. Operation of drive mechanism 116 is provided by separately powered worm gear 122.

As best illustrated in FIG. 20, the worm gear threaded portion 122 of drive shaft 130 only extends over approximately the middle third of drive shaft 130; non threaded portions 132A and 132B are provided on the proximal and distal ends of drive shaft 130 respectively, the function of which is further explained below. Positioned upon drive shaft 130 are proximal and distal drive blocks 138A and 138B. Elongated rod 140 slidingly extends through boss 144 on drive block 138B and boss 142 of drive block 138A. End stops 140A and 140B is provided at the distal ends of rod 140, the function of which will be further described below. A compression spring 146 is axially positioned upon rod 140 between boss 142 and 144 of drive blocks 138A and 138B, as best illustrated in FIG. 20, providing an axial biasing force therebetween.

When assembled in the biopsy instrument's starting or initial configuration, as illustrated in FIG. 19, the cutter drive mechanism 116 comprises drive blocks 138A and 138B positioned upon drive shaft 130 with block 138A at the far proximal end and block 138B adjacent thereto. In this configuration, block 138A rests upon the non-threaded portion 132A of drive shaft 130 and block 138B is threadingly engaged with worm gear 122. Compression spring 146 is fully compressed between bosses 142 and 144 thereby providing a maximum biasing force tending to separate drive blocks 138A and 138B. However since drive block 138B is threadingly engaged with worm gear 122 and cannot move and block 138A is being forced against collar 121 at the proximal end of drive shaft 130, the two drive blocks cannot separate.

The cutter 120 is supported by journals 148A and 148B, on drive block 138B, such that cutter drive gear 124 lies therebetween, as illustrated in FIG. 19. Thus, axial movement of drive block 138B upon worm gear 122 also causes axial movement of the cutter 120. Cutter drive gear 124 remains engaged with elongated drive gear 114 as cutter drive gear 124 advances axially toward the distal end. Cutter 120 is coaxially positioned within needle 115 along with and parallel to the specimen push rod 118 as indicated in FIGS. 20 and 21A. Specimen push rod 118 is affixed, at its proximal end, to drive block 138A as illustrated in FIG. 20. Thus as drive block 138A axially advances push rod 118 also advances. Attached to the proximal end of cutter sleeve 125 is vacuum port connector with knockout pin 126.

Alternate Embodiment—Operation

FIGS. 21, 22, and 23 illustrate the positioning of elements prior to taking a tissue sample. Drive blocks 138A and 138B are positioned at their far most proximal location as best illustrated in FIGS. 19 and 21. In this position, the cutter/specimen collection tube subassembly along with the specimen push rod are also positioned at their far most proximal location.

Figure 24:
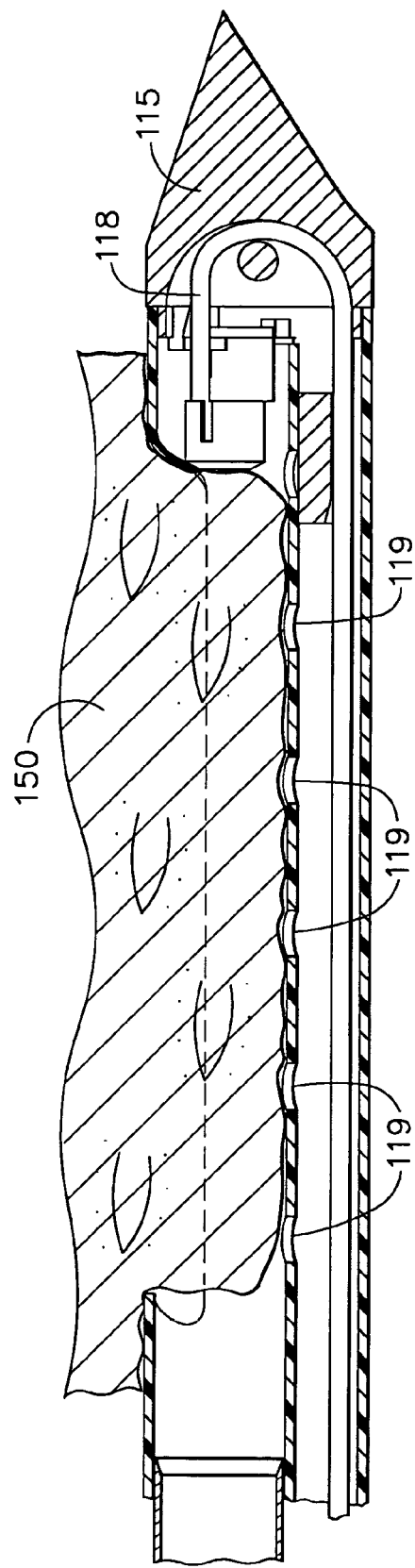
FIG. 24 presents a cross-sectional view of the distal end of the insertion needle illustrating tissue within the specimen sampling recess prior to being sampled.

To take a tissue specimen, biopsy needle 115 is inserted into the tissue to be sampled as illustrated in FIG. 24. A vacuum, supplied from vacuum tube 129 through port 128, is provided inside needle 115. Tissue 150 is drawn into specimen port 117 by action of the applied vacuum through orifices 119 in needle 115. Drive shaft 131 is rotated thereby rotating cutter 120 through the engagement of cutter drive gear 124 and drive gear 114. Simultaneously drive shaft 130 is rotated, rotating worm gear 122, whereby drive block 138B advances toward the distal end of the biopsy instrument 100. As drive block 138B advances, rotating cutter 120 also advances until drive block 138B runs off worm gear 122 and onto the non-threaded portion 132B of drive shaft 130. When drive block 138B reaches its distal end, as illustrated in FIG. 25, cutter 120 will have cut and encapsulated a sample portion of tissue 151 as shown in FIG. 27.

As drive block 138B advances onto the non-threaded portion 132B, of drive shaft 130, end stop 140B on elongated rod 140 has been advanced by the boss 144 of drive block 138B. As elongated rod 140 is advanced, end stop 140A contacts boss 142 of drive block 138A, see FIGS. 25 and 26, thereby drawing drive block 138A onto worm gear 122. As drive block 138A advances upon worm gear 122 coil spring 146 is once again placed into a compression mode thereby continuing to bias drive block 138A and 138B apart. Also as drive block 138A advances, specimen push rod 118 also advances, within lower lumen 119. And as a result of the internal curvature of the needle tip, as the specimen push rod is advanced distally within the lower lumen 119 it is deflected around the 180 degree curvature and back into the upper lumen thereby pushing specimen 151 in the proximal direction and into specimen cutter 120 as illustrated in FIG. 30.

Once drive block 138A reaches drive block 138B, as illustrated in FIGS. 28 and 29, the sampling operation is ended. Drive shaft 130 is reversed whereby drive block 138A engages with the threads on worm gear 122 by the biasing action of the compression spring 146. Drive block 138A is returned to its starting position as illustrated in FIG. 25, thereby returning specimen push rod 118 to its starting position. As drive block 138A retracts onto the non-threaded portion 132A, of drive shaft 130, elongated rod 140 has been retracted by the drive block 138A. As elongated rod 140 is retracted, end stop 140B contacts boss 144 of drive block 138B, see FIGS. 25 and 26, thereby drawing drive block 138B onto worm gear 122. As drive block 138B reverses direction, the cutter 120 also retracts.

Although it may not be necessary, it is preferred to provide a separate vacuum within cutter sleeve 125, through vacuum port connector 126 to prevent specimen 151 from moving toward the distal end of the cutter 120 under the influence of the vacuum provided within needle 115, as the specimen push rod is retracted. After all elements have been returned to their original start configuration, as illustrated in FIGS. 21, 22, and 23, the operation may be repeated to take a second specimen.

Figure 31:
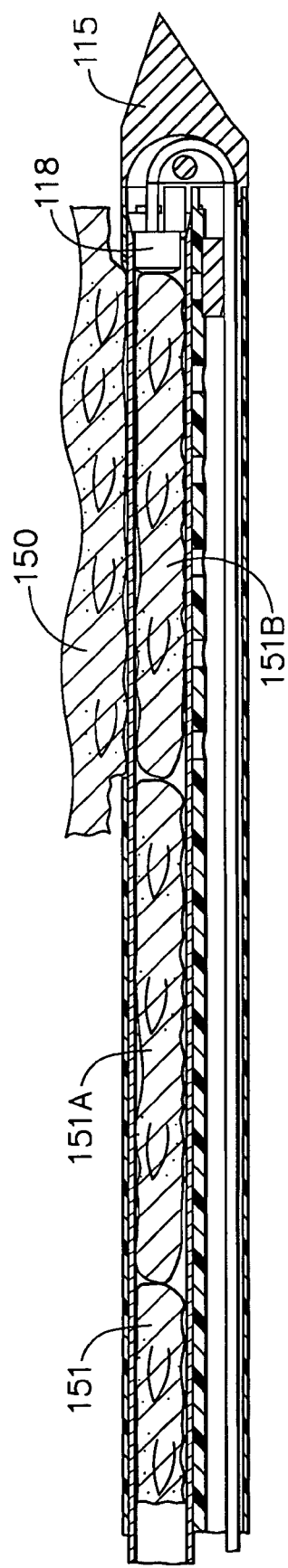
FIG. 31 presents a cross-sectional view, similar to FIGS. 24, 27 and 28, showing multiple cut tissue samples having been sequentially pushed into the cutter by the flexible push rod.

By this operation successive, multiple specimens 151, 151A, and 151B, may be taken and stored in the order taken as illustrated in FIG. 31.

By this operation successive, multiple specimens 151, 151A, and 151B, may be taken and stored in the order taken as illustrated in FIG. 31.

In the event that it is desired that each specimen be removed as it is sampled, the single specimen 151 may be drawn by vacuum to vacuum port connector 126 with integral knockout pin and withdraw upon an integral specimen catching tray extending from vacuum port connector 126 with integral knockout pin.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. It is intended that the invention be limited only by the spirit and scope of the appended claims.

We claim:
1. A handheld biopsy instrument comprising:
   a. a hollow, biopsy, insertion needle having an axially extending open specimen port at its distal end,
   b. an elongated, rotatable, tissue specimen cutter slidably received within said biopsy insertion needle, wherein the cutter has a distal end,
   c. an elongated flexible push rod slidably received within said needle and parallel to said cutter, said push rod extending to the distal end of said needle,
   d. means for applying a first vacuum within the distal end of said needle whereby a portion of a tissue to be sampled is drawn into said specimen port when said needle is inserted into the tissue to be sampled,
   e. means for advancing said cutter toward the distal end of said needle,
   f. means for rotating said cutter as said cutter advances within said needle, whereby said cutter cuts and encapsulates the portion of said tissue contained within said specimen port,
   g. means for advancing said flexible push rod axially toward the distal end of said needle, and
   h. means at the distal end of said needle for causing said push rod to turn 180 degrees thereby reversing its direction of movement from a distal direction to a proximal direction, whereby said push rod end enters said cutter from the distal end of the cutter, engages said encapsulated tissue specimen therein, thereby moving said tissue specimen axially toward the proximal end of said cutter.

2. The biopsy instrument of claim 1 wherein the biopsy insertion needle comprises an upper lumen and a lower lumen.

3. The biopsy instrument of claim 2 wherein the distal end of the cutter is received within the upper lumen.

4. The biopsy instrument of claim 2 wherein at least a portion of the push rod is slidably received in the lower lumen.

5. The biopsy instrument of claim 4 wherein the lower lumen communicates with a source of vacuum.

6. The biopsy instrument of claim 1 comprising a specimen collection tube, and wherein the specimen tube is removable from the biopsy instrument.

7. The biopsy instrument of claim 1 comprising a specimen collection tube, and wherein the specimen collection tube and the cutter are configured to advance and retract in unison.

8. A handheld biopsy instrument comprising:
   a biopsy needle having a tissue piercing distal tip and a tissue receiving port disposed proximal of the tissue piercing distal tip, wherein the biopsy needle further comprises a first lumen for receiving a hollow cutter, and a second lumen, wherein the second lumen is external to and parallel to the first lumen, wherein the tissue receiving port is in communication with the first lumen;

the hollow cutter having a distal end, wherein the distal end of the cutter is slidably received within the first lumen of the biopsy needle, and wherein the cutter is rotatable and translatable within the first lumen of the biopsy needle for severing tissue received in the tissue receiving port of the biopsy needle;

an elongated flexible push rod, wherein at least a portion of the push rod is slidably received with the second lumen of the needle and extends external to and parallel to the cutter, and wherein a distal end of the elongated flexible push rod is adapted to push a tissue sample in a proximal direction into the hollow cutter in response to distal pushing on a proximal portion of the elongated flexible push rod; and a specimen tube for receiving tissue severed by the hollow cutter.

9. A handheld biopsy instrument comprising:

a biopsy needle having a tissue piercing distal tip and a tissue receiving port disposed proximal of the tissue piercing distal tip;

a hollow cutter having a distal end, wherein the distal end of the cutter is slidably received within the biopsy needle, and wherein the cutter is rotatable and translatable within the biopsy needle for severing tissue received in the tissue receiving port of the biopsy needle;

a flexible push rod, wherein a portion of the flexible push rod is adapted to move distally within the needle, and wherein a distal end of the flexible push rod is adapted to push a tissue sample in a proximal direction into the hollow cutter in response to distal pushing on a proximal portion of the flexible push rod.

10. The biopsy instrument of claim 9 wherein the biopsy insertion needle comprises an upper lumen and a lower lumen.

11. The biopsy instrument of claim 10 wherein the distal end of the cutter is received within the upper lumen.

12. The biopsy instrument of claim 10 wherein at least a portion of the flexible push rod is slidably received in the lower lumen.

13. The biopsy instrument of claim 9 wherein the distal end of the flexible push rod is turned about 180 degrees during operation of the biopsy instrument.

14. The biopsy instrument of claim 9 further comprising a specimen receiver wherein the specimen receiver is removable from the biopsy instrument.

15. The biopsy instrument of claim 14 wherein the specimen receiver and the cutter are configured to advance and retract in unison.

* * * * *